United States Patent
Watts et al.

(10) Patent No.: US 12,011,298 B2
(45) Date of Patent: Jun. 18, 2024

(54) MEMBRANE-BASED FOOT IMAGING APPARATUS INCLUDING A CAMERA FOR MONITORING FOOT POSITIONING

(71) Applicant: CRYOS TECHNOLOGIES INC., Joliette (CA)

(72) Inventors: Gregory Nicholas Watts, Joliette (CA); Mohamed Lachhab, Joliette (CA); Patrick Mougin, Rawdon (CA); Philippe Légaré, Joliette (CA); Frédéric Gremillet, Joliette (CA)

(73) Assignee: CRYOS TECHNOLOGES INC., Joliette (CA)

( * ) Notice: Subject to any disclaimer, the term of this patent is extended or adjusted under 35 U.S.C. 154(b) by 1175 days.

(21) Appl. No.: 16/093,524

(22) PCT Filed: Nov. 22, 2016

(86) PCT No.: PCT/CA2016/051366
§ 371 (c)(1),
(2) Date: Oct. 12, 2018

(87) PCT Pub. No.: WO2017/177304
PCT Pub. Date: Oct. 19, 2017

(65) Prior Publication Data
US 2019/0209093 A1    Jul. 11, 2019

Related U.S. Application Data

(60) Provisional application No. 62/321,818, filed on Apr. 13, 2016.

(51) Int. Cl.
*A61B 5/00* (2006.01)
*A61B 5/103* (2006.01)
*A61B 5/107* (2006.01)

(52) U.S. Cl.
CPC .............. *A61B 5/706* (2013.01); *A61B 5/004* (2013.01); *A61B 5/0077* (2013.01);
(Continued)

(58) Field of Classification Search
CPC ....... A61B 5/706; A61B 5/004; A61B 5/0077; A61B 5/0082; A61B 5/1036; A61B 5/1074; A61B 5/1078; A61B 5/1079; A61B 5/70
See application file for complete search history.

(56) References Cited

U.S. PATENT DOCUMENTS 5,088,503 A    2/1992    Seitz
5,689,446 A  * 11/1997    Sundman ............. A61B 5/1074
                                                  702/167
(Continued)

FOREIGN PATENT DOCUMENTS

CA    2730475 A1    1/2010
CA    2888468 A1    4/2014
(Continued)

OTHER PUBLICATIONS

International Search Report and Written Opinion, dated Dec. 30, 2016, issued in International Application No. PCT/CA2016/051366.
(Continued)

*Primary Examiner* — Ashley K Buran
*Assistant Examiner* — Helene Bor
(74) *Attorney, Agent, or Firm* — Barnes & Thornburg LLP

(57) ABSTRACT

A foot imaging apparatus includes a support structure and a flexible membrane suspended from the support structure and configured to receive a foot thereon. The apparatus also includes a three-dimensional imager located under the flexible membrane and configured to acquire a topographical (Continued)

plantar image of the foot on the flexible membrane. The apparatus further includes a monitoring unit for monitoring a monitored region in order to evaluate a positioning of the foot on the flexible membrane. The monitoring unit includes a camera having a field of view, and at least one light deflector arranged to deflect light from the monitored region into the field of view of the camera. The camera acquires a monitoring image of the monitored region after deflection by the at least one light deflector. The monitoring image contains information about the positioning of the foot on the flexible membrane. A foot imaging method is also provided.

27 Claims, 24 Drawing Sheets

(52) U.S. Cl.
CPC .......... *A61B 5/0082* (2013.01); *A61B 5/1036* (2013.01); *A61B 5/1074* (2013.01); *A61B 5/1078* (2013.01); *A61B 5/1079* (2013.01); *A61B 5/70* (2013.01)

(56) References Cited

U.S. PATENT DOCUMENTS

| | | | | |
|---|---|---|---|---|
| 6,205,230 | B1* | 3/2001 | Sundman | G01B 21/20 |
| | | | | 382/100 |
| 6,549,639 | B1* | 4/2003 | Genest | A61B 5/1074 |
| | | | | 382/285 |
| 6,829,377 | B2 | 12/2004 | Milioto | |
| 7,068,379 | B2 | 6/2006 | Sundman et al. | |
| 7,262,862 | B2* | 8/2007 | Klaveness | A61B 5/1078 |
| | | | | 356/601 |
| 7,392,559 | B2 | 7/2008 | Peterson | |
| 7,552,494 | B2 | 6/2009 | Peterson | |
| 7,657,054 | B2 | 2/2010 | Phillips | |
| 7,952,727 | B2 | 5/2011 | Sundman et al. | |
| 8,567,081 | B2* | 10/2013 | Smith | A61B 5/6829 |
| | | | | 33/515 |
| 2001/0030297 | A1* | 10/2001 | Milioto | A61B 5/1077 |
| | | | | 250/559.22 |
| 2003/0212506 | A1* | 11/2003 | Sundman | A61B 5/1077 |
| | | | | 702/40 |
| 2006/0076700 | A1 | 4/2006 | Phillips | |
| 2006/0098896 | A1* | 5/2006 | Pishdadian | G01B 11/24 |
| | | | | 382/154 |
| 2006/0103852 | A1 | 5/2006 | Klaveness | |
| 2006/0227337 | A1* | 10/2006 | Sundman | A43D 1/025 |
| | | | | 356/601 |
| 2006/0283243 | A1* | 12/2006 | Peterson | A61B 5/1036 |
| | | | | 73/172 |
| 2009/0076772 | A1* | 3/2009 | Hinshaw | A43D 1/025 |
| | | | | 36/43 |
| 2011/0313321 | A1* | 12/2011 | Alfaro Santafe | A61B 5/103 |
| | | | | 600/587 |
| 2014/0098896 | A1* | 4/2014 | Wang | H04N 19/46 |
| | | | | 375/240.26 |
| 2014/0104395 | A1* | 4/2014 | Rohaly | G01B 11/165 |
| | | | | 348/47 |
| 2014/0121532 | A1* | 5/2014 | O'Connor | A61B 5/1074 |
| | | | | 600/476 |
| 2014/0276094 | A1 | 9/2014 | Lidtke | |

FOREIGN PATENT DOCUMENTS

| | | |
|---|---|---|
| WO | 03/087717 A1 | 10/2003 |
| WO | 2015/176183 A1 | 11/2015 |
| WO | WO 2015/176183 A1 | 11/2015 |

OTHER PUBLICATIONS

International Search Report and Written Opinion, issued in International Application No. PCT/CA2016/051366, 10 pages (dated Dec. 30, 2016).
"Cinderella Ski Boot Fit", post by WildSnow.com blogger, Lisa Dawson, pp. 63, The Backcountry Skiing Blog (Nov. 14, 2012).

* cited by examiner

Membrane with foot
received theron
(28)

Reflection of the
membrane with foot
received theron
(70)

MEMBRANE-BASED FOOT IMAGING APPARATUS INCLUDING A CAMERA FOR MONITORING FOOT POSITIONING

RELATED APPLICATIONS

The present application is a national stage application under 35 U.S.C. § 371 of International Patent Application No. PCT/CA2016/051366, filed Nov. 22, 2016, and which claims priority from U.S. Provisional Application No. 62/321,818, filed Apr. 13, 2016. The above-referenced applications are hereby incorporated by reference into the present application in their entirety.

TECHNICAL FIELD

The general technical field relates to imaging techniques for acquiring a three-dimensional (3D) image of a foot and, in particular, to techniques for monitoring a foot received on a membrane of a 3D foot imaging apparatus to assess correct positioning of the foot during the image acquisition process.

BACKGROUND

Various techniques exist for measuring the 3D shape of the plantar surface of a foot to produce patent-specific orthoses. Traditional techniques generally involve forming a mold of the patient's foot (e.g., a plaster cast or a foam box impression), a long and materially expensive process, and then shipping this mold to an orthotic laboratory to be used to create the prescribed orthoses. Despite certain advantages in terms of simplicity and cost, casting techniques can be time consuming and labor intensive, which limit the number of patients that a practitioner can treat daily.

In recent years, optical imaging and scanning techniques have become more ubiquitous in the podiatric environment and have been used to acquire the 3D plantar foot shape as clinicians seek to harness the increase in efficiency that comes with their use. These techniques can allow the same information as in traditional techniques to be quickly and cleanly captured by the podiatrist, podiatric physician or another healthcare professional using a 3D scanner (e.g., a digital laser scanner) and transferred to the orthotic laboratory almost in real-time. At the orthotic laboratory, the transferred image data can be used in a computer-aided design and manufacturing (CAD/CAM) system to design and fabricate patient-specific orthoses. Optical imaging and scanning techniques can provide time and cost advantages over traditional casting and molding techniques. Depending on the intended application, optical imaging and scanning techniques can allow 3D plantar images to be acquired in any of a non-weight-bearing, full-weight-bearing and semi-weight-bearing state, each having its own challenges and limitations.

For example, measurement techniques that acquire an image of the foot in a non-weight-bearing state generally cannot account for the natural elongation and deformation of the foot that occur when weight is applied thereto, which can lead to unreliable measurements. In contrast, in a full-weight-bearing condition, the deformation imposed on the foot can become significant enough to negatively affect the reliability of the scanned image, notably arch measurements. It can also be difficult to position the foot in a neutral position in a full-weight-bearing condition. A semi-weight-bearing condition can provide an intermediate and, in principle, more accurate configuration to acquire an image of the plantar surface, as this condition is often more representative of the natural elongation and deformation of the foot in the walking stance.

Acquiring a 3D plantar image with the foot in a semi-weight-bearing state is not straightforward, as achieving proper soft tissue deformation requires careful positioning of the foot, which can prove challenging using existing techniques. As with traditional techniques, a desirable and often essential characteristic of a "good mold" or "good scan" is that the forefoot and rearfoot be positioned and aligned appropriately. With 3D scanning techniques, this typically involves having the forefoot positioned relatively flat and parallel to a ground or reference plane. This condition can be difficult to achieve as the forefoot is typically not easily visible to the operator during the image capture or scanning process.

Accordingly, many challenges remain in the development of techniques for acquiring 3D plantar images in the semi-weight-bearing condition while ensuring that the foot is adequately positioned during the image acquisition process.

SUMMARY

The present description generally relates to techniques for monitoring a foot received on a flexible membrane of a foot imaging apparatus for determining whether the foot is correctly positioned prior to acquiring a topographical plantar image of the foot with a 3D imager of the foot imaging apparatus.

In accordance with an aspect, there is provided a foot imaging apparatus including:
- a support structure;
- a flexible membrane suspended from the support structure and configured to receive a foot thereon;
- a three-dimensional (3D) imager located under the flexible membrane and configured to acquire a topographical plantar image of the foot on the flexible membrane; and
- a monitoring unit for monitoring a monitored region in order to evaluate a positioning of the foot on the flexible membrane, the monitoring unit including a camera having a field of view, and at least one light deflector arranged to deflect light from the monitored region into the field of view of the camera, the camera acquiring a monitoring image of the monitored region after deflection by the at least one light deflector, the monitoring image containing information about the positioning of the foot on the flexible membrane.

In some implementations, the camera and the at least one light deflector are arranged with respect to the flexible membrane such that the monitoring image provides one of a front elevation view and a rear elevation view of the foot received on the flexible membrane.

In some implementations, the camera and the at least one light deflector are arranged with respect to the flexible membrane such that the monitoring image provides at least one of a view of the flexible membrane with the foot thereon and a view of a reflection of the flexible membrane with the foot thereon.

In some implementations, the foot imaging apparatus includes a housing having a top wall, a bottom wall, and a sidewall interconnecting the top and bottom walls, the top wall having an opening therein enclosed by the support structure such that the flexible membrane extends across the opening.

In some implementations, the bottom wall is mounted on a top surface of the 3D imager, the at least one light deflector is located inside the housing, and the camera is located inside the 3D imager and configured to acquire the monitoring image through the bottom wall of the housing and the top surface of the 3D imager.

In some implementations, the 3D imager is located inside the housing.

In some implementations, the at least one light deflector is a plane mirror lying at least partly in the field of view of the camera.

In some implementations, the plane mirror has a surface normal that is oriented at a tilt angle with respect to an axis of the field of view of the camera.

In some implementations, the axis of the field of view of the camera points vertically upward and the tilt angle is equal to 45°.

In some implementations, the tilt angle ranges from 30° to 60°.

In some implementations, the tilt angle is equal to 45°.

In some implementations, the axis of the field of view of the camera points vertically upward.

In some implementations, the monitoring image is a still image.

In some implementations, the monitoring image is a video stream.

In some implementations, the camera is configured to output the monitoring image to a visual display device.

In some implementations, the foot imaging apparatus further includes a visual display device configured to display the monitoring image acquired by the camera.

In some implementations, the information about the positioning of the foot received on the flexible membrane includes one or more of the following: a degree of flatness of a forefoot-receiving region of the flexible membrane with the foot received thereon; a presence or absence of physical contact between the flexible membrane with the foot received thereon and an underlying solid surface; a degree of deformation of the front portion of the foot when the foot is received on the flexible membrane; a degree of dorsiflexion of the toes when the foot is received on the flexible membrane; and a position of the foot with respect to reference markers.

In some implementations, the flexible membrane is configured to receive the foot thereon in a semi-weight-bearing condition.

In accordance with another aspect, there is provided a foot imaging apparatus including:
  a support structure;
  a flexible membrane suspended from the support structure and configured to receive a foot thereon;
  a three-dimensional (3D) imager located under the flexible membrane and configured to acquire a topographical plantar image of the foot on the flexible membrane; and
  a monitoring unit for monitoring a monitored region in order to evaluate a positioning of the foot on the flexible membrane, the monitoring unit including a camera configured to acquire a monitoring image of the monitored region, the monitoring image containing information about the positioning of the foot on the flexible membrane and corresponding to one of a front view and a rear view of the foot received on the flexible membrane.

In some implementations, the foot imaging apparatus further includes at least one light deflector arranged to deflect light from the monitored region into a field of view of the camera for capture by the camera as the monitoring image.

In accordance with another aspect, there is provided a foot imaging apparatus including:
  a support structure;
  a flexible membrane suspended from the support structure and configured to receive a foot thereon;
  a three-dimensional (3D) imager located under the flexible membrane and configured to acquire a topographical plantar image of the foot on the flexible membrane; and
  a monitoring unit for monitoring a monitored region in order to evaluate a positioning of the foot on the flexible membrane, the monitoring unit including a camera having a field of view, and a light deflector lying at least partly in the field of view of the camera and arranged to deflect light from the monitored region toward the camera, the camera acquiring a monitoring image of the monitored region after deflection by the light deflector, the monitoring image containing information about the positioning of the foot on the flexible membrane.

In some implementations, the light deflector is a plane mirror.

In accordance with another aspect, there is provided a foot imaging apparatus including:
  a support structure;
  a flexible membrane suspended from the support structure and configured to receive a foot thereon;
  a three-dimensional (3D) imager located under the flexible membrane and configured to acquire a topographical plantar image of the foot on the flexible membrane; and
  a monitoring unit for monitoring a monitored region in order to evaluate a positioning of the foot on the flexible membrane, the monitoring unit including:
    a first camera having a first field of view, and a first light deflector lying at least partly in the first field of view and arranged to deflect light from the monitored region toward the first camera, the first camera acquiring a monitoring image of the monitored region after deflection by the light deflector, the monitoring image containing information about the positioning of the foot on the flexible membrane and corresponding to a front view of the foot received on the flexible membrane; and
    a second camera having a second field of view, and a second light deflector lying at least partly in the second field of view and arranged to deflect light from the monitored region toward the second camera, the second camera acquiring a monitoring image of the monitored region after deflection by the light deflector, the monitoring image containing information about the positioning of the foot on the flexible membrane and corresponding to a rear view of the foot received on the flexible membrane.

In accordance with another aspect, there is provided a membrane assembly including:
  a housing having a top wall, a bottom wall, and a sidewall interconnecting the top and bottom walls, the top wall having an opening therein;
  a support structure arranged along a periphery of the opening;
  a flexible membrane suspended from the support structure across the opening and configured to receive a foot thereon; and
  a monitoring unit inside the housing for monitoring a monitored region in order to evaluate a positioning of the foot on the flexible membrane, the monitoring unit including a camera configured to acquire a monitoring image of the monitored region, the monitoring image containing information about the positioning of the foot on the flexible membrane and corresponding to one of a front view and a rear view of the foot received on the flexible membrane.

In some implementations, the membrane assembly further includes at least one light deflector arranged to deflect light from the monitored region into a field of view of the camera for capture by the camera as the monitoring image.

In accordance with another aspect, there is provided a membrane assembly for monitoring a positioning of a foot, the membrane assembly including:
- a housing having a top wall, a bottom wall, and a sidewall interconnecting the top and bottom walls, the top wall having an opening therein;
- a support structure arranged along a periphery of the opening;
- a flexible membrane suspended from the support structure across the opening and configured to receive a foot thereon; and
- a monitoring unit inside the housing for monitoring a monitored region in order to evaluate a positioning of the foot on the flexible membrane, the monitoring unit including a camera having a field of view, and a light deflector lying at least partly in the field of view of the camera and arranged to deflect light from the monitored region toward the camera, the camera acquiring a monitoring image of the monitored region after deflection by the light deflector, the monitoring image containing information about the positioning of the foot on the flexible membrane.

In accordance with another aspect, there is provided a membrane assembly for use with a three-dimensional imager to obtain a topographical plantar image of a foot, the membrane assembly including:
- a housing having a top wall, a bottom wall, and a sidewall interconnecting the top and bottom walls, the top wall having an opening therein;
- a support structure arranged along a periphery of the opening;
- a flexible membrane suspended from the support structure across the opening and configured to receive a foot thereon, the three-dimensional imager being positionable under the flexible membrane to acquire the topographical plantar image when the foot is disposed on the flexible membrane; and
- a monitoring unit inside the housing for monitoring a monitored region in order to evaluate a positioning of the foot on the flexible membrane, the monitoring unit including a camera configured to acquire a monitoring image of the monitored region, the monitoring image containing information about the positioning of the foot on the flexible membrane and corresponding to one of a front view and a rear view of the foot received on the flexible membrane.

In accordance with another aspect, there is provided a method for imaging a foot, including the steps of:
- providing a suspended flexible membrane;
- disposing the foot on the flexible membrane;
- monitoring a positioning of the foot on the flexible membrane, including acquiring a monitoring image containing information about the positioning of the foot on the flexible membrane;
- analyzing the monitoring image to determine whether the positioning of the foot on the flexible membrane is correct; and
- if the positioning of the foot on the flexible membrane is correct, acquiring a topographical plantar image of the foot received on the flexible membrane; otherwise, adjusting the positioning of the foot on the flexible membrane and repeating the monitoring, analyzing and adjusting steps until the positioning of the foot on the flexible membrane is correct.

In some implementations, acquiring the monitoring image includes providing one of a front elevation view and a rear elevation view of the foot received on the flexible membrane.

In some implementations, acquiring the monitoring image includes providing at least one of a view of the flexible membrane with the foot thereon and a view of a reflection of the flexible membrane with the foot thereon.

In some implementations, analyzing the monitoring image includes assessing at least one of: a degree of flatness of a forefoot-receiving region of the flexible membrane with the foot received thereon; a presence or absence of physical contact between the flexible membrane with the foot received thereon and an underlying solid surface; a degree of deformation of the front portion of the foot when the foot is received on the flexible membrane; a degree of dorsiflexion of the toes when the foot is received on the flexible membrane; and a position of the foot with respect to reference markers.

In accordance with another aspect, there is provided a method for monitoring a positioning of a foot on a suspended flexible membrane, including the steps of:
- placing the foot on the suspended flexible membrane;
- monitoring a positioning of the foot on the flexible membrane, including acquiring a monitoring image containing information about the positioning of the foot on the flexible membrane;
- analyzing the monitoring image to determine whether the positioning of the foot on the flexible membrane is correct; and
- if the positioning of the foot on the flexible membrane is incorrect, adjusting the positioning of the foot on the flexible membrane and repeating the monitoring, analyzing and adjusting steps until the positioning of the foot on the flexible membrane is correct.

In accordance with another aspect, there is provided a use of the membrane assembly as described herein, in combination with a 3D imager, for monitoring correct foot positioning during the acquisition of a topographical plantar image of a foot.

In accordance with another aspect, there is provided a use of the foot imaging apparatus as described herein for monitoring correct foot positioning during the acquisition of a topographical plantar image of a foot.

Other features and advantages of aspects of the techniques described herein will be better understood upon reading of preferred embodiments thereof with reference to the appended drawings.

BRIEF DESCRIPTION OF THE DRAWINGS

As shown in FIG. 3 the apparatus includes thereinside a monitoring unit for monitoring the foot whose topographical plantar image is to be acquired when the foot is received on the membrane and for determining whether the foot is correctly positioned on the flexible membrane.

FIG. 4 is the same as FIG. 3, but with the foot received on the flexible membrane.

In FIG. 9A, only the foot-receiving membrane is monitored by the monitoring unit.

In FIG. 9B, only a reflection of the foot-receiving membrane is monitored by the monitoring unit.

In FIG. 10A, the monitoring unit includes a camera but no light deflector.

In FIG. 11, the monitoring unit monitors the rear portion of the foot.

In FIG. 12, the monitoring unit includes two cameras and two light deflectors.

In FIG. 13A, the monitoring unit includes a camera and a light deflector that are both provided inside the membrane assembly.

In FIG. 14A, the monitoring image indicates that the positioning of the foot on the membrane is correct.

In FIG. 14B, the monitoring image indicates that the positioning of the foot on the membrane is incorrect.

In FIG. 15A, only the foot-receiving membrane is visible on the monitoring image.

In FIG. 15B, only the reflection of the foot-receiving membrane is visible on the monitoring image.

In FIG. 17, the monitoring image indicates that the positioning of the foot on the membrane is correct.

In FIG. 19, the monitoring unit includes a camera located in the 3D imager and two light deflectors associated with the camera and located both in the membrane assembly.

DETAILED DESCRIPTION

Figure 1:
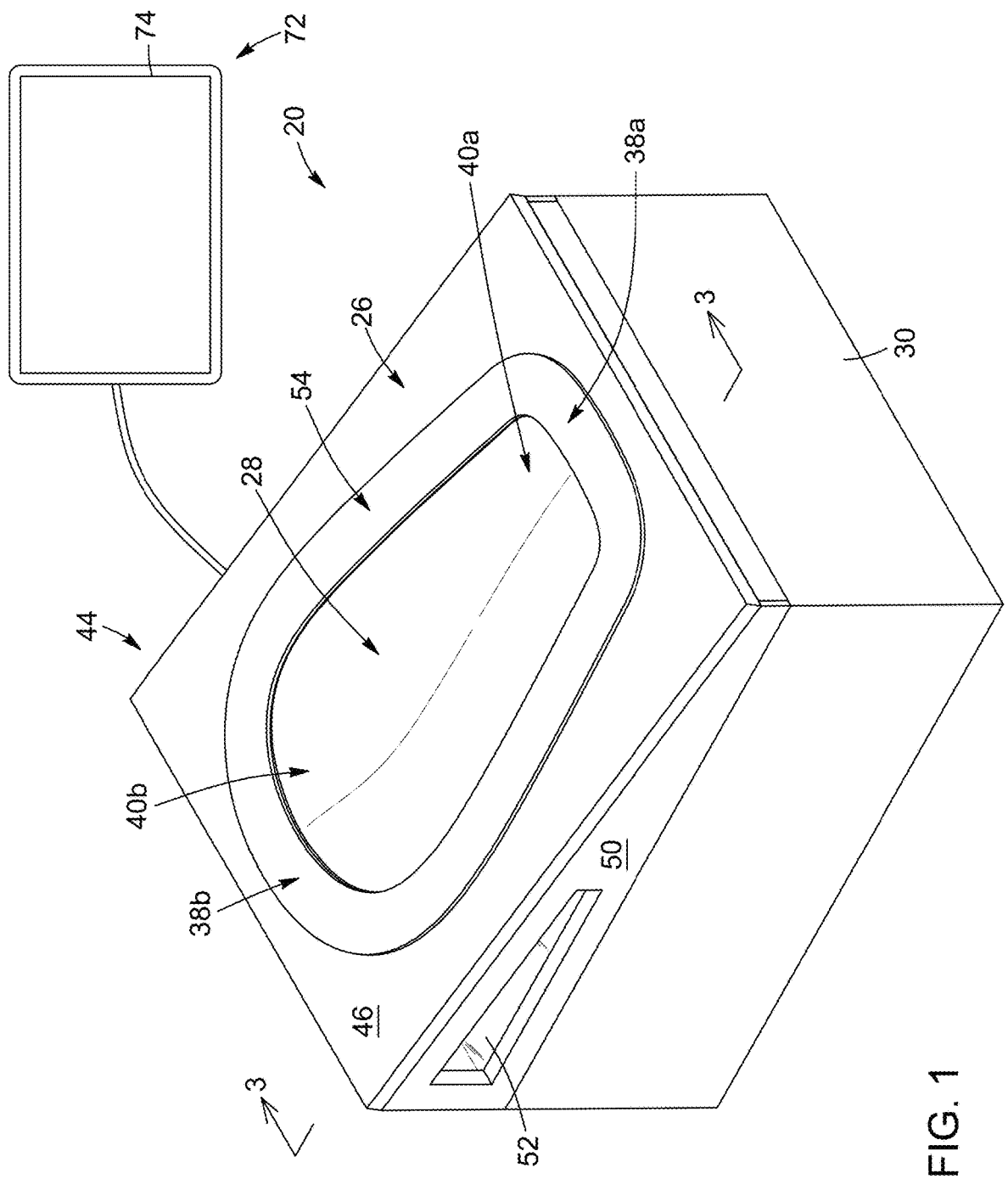
FIG. 1 is a perspective view of a foot imaging apparatus, in accordance with an exemplary embodiment.
Figure 2:
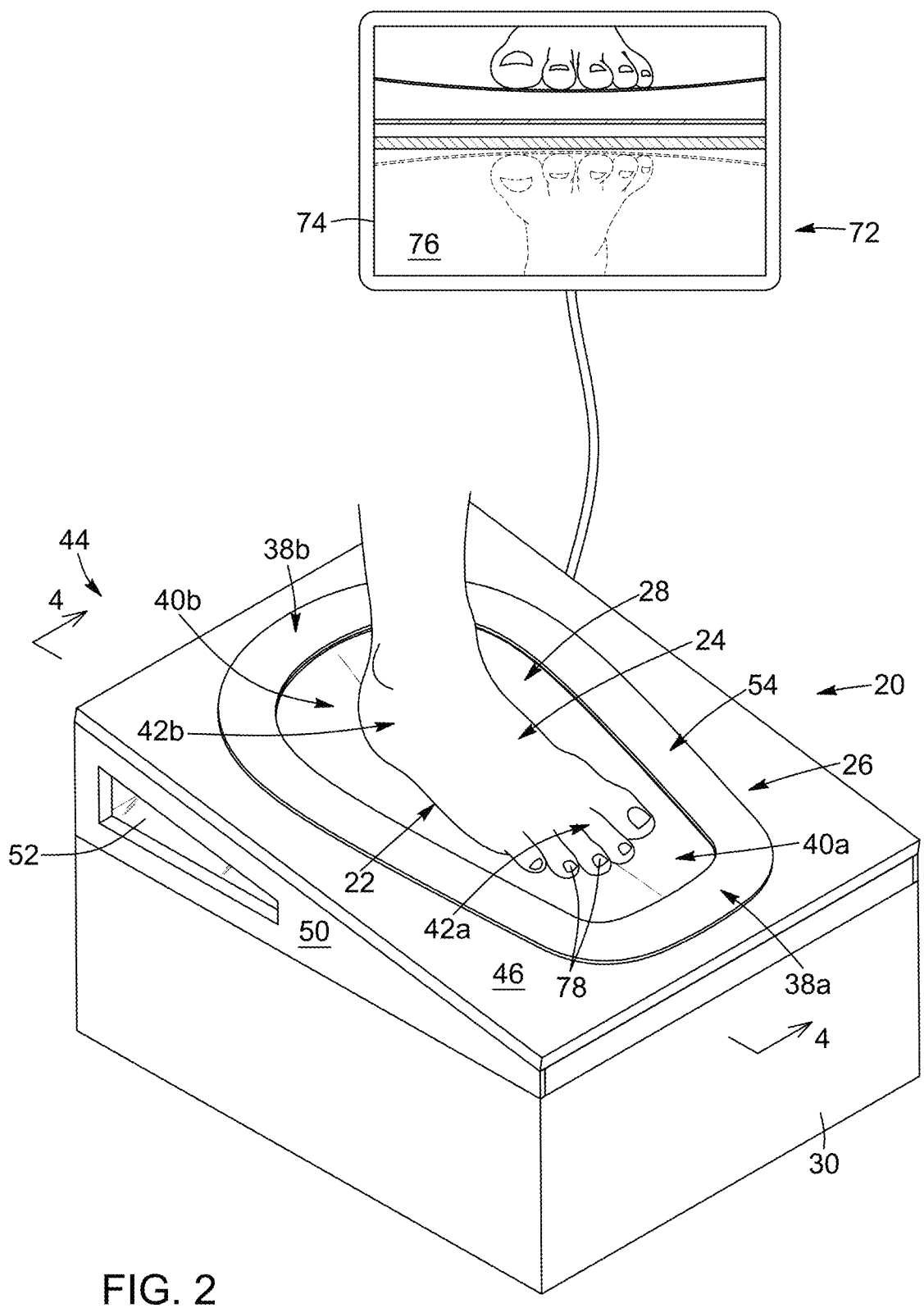
FIG. 2 is the same as FIG. 1, but with a foot received on the flexible membrane.

In the following description, similar features in the drawings have been given similar reference numerals, and, to not unduly encumber the figures, some elements may not be indicated on some figures if they were already identified in preceding figures. It should also be understood herein that the elements of the drawings are not necessarily depicted to scale, since emphasis is placed upon clearly illustrating the elements and structures of the present embodiments.

The present description generally relates to techniques for obtaining a topographical plantar image of a foot in which proper foot positioning for the image acquisition process is monitored and assessed. More particularly, the present description relates to techniques for monitoring a foot received and supported on a suspended flexible membrane of a 3D foot imaging apparatus to ensure or help ensure correct foot positioning for image acquisition by a 3D imager of the foot imaging apparatus.

In the present techniques, the 3D foot imaging apparatus can include, among other components, a monitoring unit including at least one camera and configured to monitor the foot received on the flexible membrane, for example in a semi-weight-bearing condition, and to assess whether the foot is correctly positioned on the membrane prior to acquiring the topographical plantar image of the foot using the 3D imager of the imaging apparatus. In accordance with different non-limiting aspects of the techniques described herein, there is provided a foot imaging apparatus including a membrane assembly, a 3D imager and a monitoring unit; a membrane assembly for use with a 3D imager and including a monitoring unit; and a method for imaging a foot.

As used herein, the term "foot positioning", when used in relation with a foot received on a flexible membrane, is to be interpreted broadly to describe the physical disposition and arrangement of the foot relative to itself and relative to the membrane including, without limitation, its location, orientation, distance, direction, alignment, and deformation. Different methods and criteria (both objective and subjective) can be used to determine whether foot positioning is correct. By way of example, in some implementations, criteria that can be used to determine whether the foot is positioned correctly on the membrane can include, without limitation:

- assessing whether a portion of the foot disposed on the membrane impinges on and bears against an underlying solid surface;
- assessing whether the forefoot-receiving region of the membrane presents a sufficiently uniform and flat receiving surface to the forefoot;
- assessing whether the deformation of the forefoot due to vertical and/or lateral compressive loads remains sufficiently small;
- assessing whether the toes are not overly curled up; and
- assessing the position, orientation and/or alignment of the foot with respect to reference markers (e.g., reference points or planes).

As used herein, the term "topographical plantar image" and variants thereof broadly refer to a 3D relief map or model replicating the plantar foot surface in a certain weight-bearing condition. The topographical plantar image generally includes an array of 3D data points, where each data point can be described by its spatial coordinate Z(x, y), where Z is the local height or elevation of the surface at location (x, y). As described below, a topographical image of the plantar foot surface can be acquired using optical methods, for example 3D laser scanners and 3D digital stereo imaging systems. In the present description, the term "topographical plantar image" may be used interchangeably with the term "3D plantar image". Also, the term "plantar surface" as used herein has its ordinary meaning and refers to the underside or bottom surface of the foot.

As known in the art, topographical plantar images can be acquired with the foot in three main weight-bearing conditions: non-weight-bearing, full-weight-bearing and semi-weight-bearing. The term "non-weight-bearing" refers to a condition where no body weight is applied to the foot, as if the foot were in suspension. The term "full-weight-bearing" refers to a weight-bearing condition where the foot supports the entire body weight. The term "semi-weight-bearing" refers to a weight-bearing condition where only a certain amount of body weight is supported by the foot, such as, for example, between 20% and 50% of the total body weight. Of course, this range is provided for exemplary purposes only, such that values lying outside this range can be used in certain embodiments. In the present description, the terms "semi-weight bearing" and "partial-weight bearing" can be used interchangeably.

In some instances, acquiring a 3D plantar image with the foot in a semi-weight-bearing state may be desirable or even necessary. One reason is that the amount of soft tissue deformation under semi-weight bearing can be controlled more accurately and be more representative of the natural physiological deformation of the foot under the weight of the body, for example the height of the medial and lateral longitudinal arches and the natural deformation of the foot axis. Measuring the 3D plantar shape under some controlled level of deformation under semi-weight bearing can be beneficial, while an absence or excess of deformation, as in non-weight-bearing and full-weight-bearing conditions, can lead to inaccuracies in the measured data. It is to be noted that the techniques described herein can be applied to monitor foot positioning not only in a semi-weight-bearing state, but also in non-weight-bearing and full-weight-bearing conditions.

Acquiring a 3D plantar image in a semi-weight-bearing condition can be challenging and can involve carefully selecting the structure and configuration of the flexible membrane and/or its support structure by providing, for example:

- a foot-receiving surface that is not locally deformed by another physical part of the system (e.g., a plate-like surface) when the foot is received thereon;
- a controlled pressure exerted on the foot that is adapted to the flexibility and dimensions of the foot, and that induces a deformation of the foot that is anatomically similar to the natural physiological deformation of the foot under the weight of the body; and
- a configuration that can remain stable over the entire duration of the image acquisition process.

A general aim of some of the present techniques is to monitor, using a dedicated monitoring camera, whether a foot to be imaged is correctly positioned on a foot-receiving membrane prior to and during the image acquisition process.

In some implementations, the monitoring camera is positioned and configured to monitor the front region of the foot (i.e., the forefoot). This is because controlling the forces exerted on the forefoot by the flexible membrane can reduce or help reduce the deformation of the forefoot which, if significant, can have repercussions on the overall shape of the plantar surface and, potentially, degrade the reliability and accuracy of the 3D plantar image. More particularly, it is generally desirable that the toes are neither excessively dorsiflexed (i.e., not overly curled up) nor forming artificial longitudinal arches (i.e., either concave or convex), to ensure that the medial and lateral arches, whose shape is to be acquired, are not adversely deformed. At the same time, a certain amount of deformation in the rear foot region may be beneficial, especially as it can allow the 3D plantar image to be more representative of the natural physiological deformation of the medial and lateral arches.

In some implementations, a live video stream of the forefoot acquired by the monitoring camera can be displayed to the operator (e.g., a podiatrist, podiatric physician or another healthcare professional) on a visual display device (e.g., a computer monitor) to provide the operator with instant feedback on the positional configuration of the foot received on the flexible membrane. Such implementations can allow more accurate and rapid positioning of the forefoot on the suspended membrane, and can reduce, sometimes significantly, the number of rescans required (i.e., the number of trial and error scans to get correct foot positioning).

Foot Imaging Apparatus

In accordance with an aspect, there is provided a foot imaging apparatus 20 configured for obtaining a topographical image of a plantar surface 22 of a foot 24, an exemplary embodiment of which is illustrated in FIGS. 1 to 6.

Broadly described, this embodiment of the foot imaging apparatus 20 includes a support structure 26; a flexible membrane 28 suspended from the support structure 26 and configured to receive the foot 24 thereon; a 3D imager 30 located under the flexible membrane 28 to acquire a topographical plantar image of the foot 24 when the foot 24 is placed on the membrane 28 (see FIGS. 2, 4 and 6); a monitoring unit for monitoring a foot positioning on the membrane 28. The monitoring unit 32 includes a camera 34 having a field of view 35, and a light deflector 36 (see FIGS. 3 and 4) arranged to deflect an image indicative of the foot positioning onto and for capture by the camera 34. The image indicative of the foot positioning can be referred to herein as a "monitoring image". More details regarding the structure, configuration and operation of these and other possible components of the foot imaging apparatus 20 will be described in greater detail below.

Support Structure

As used herein, the term "support structure" refers broadly to any structure that can hold and mechanically support the flexible membrane, generally via its periphery, in a manner such that the flexible membrane hangs from the support structure and can support a foot received thereon. In the embodiment of FIGS. 1 to 6, the support structure 26 includes a front end 38a and a rear end 38b elevated relative to the front end 38a. As used herein, the term "elevated" refers to the rear end of the support structure being vertically higher than the front end when measured upwardly from the bottom of the foot imaging apparatus. By way of example, in some embodiments, the elevation angle of the rear end 38b of the support structure 26 relative to the front end 38a thereof ranges between about 5 degrees (°) and about 30°, and in other embodiments, the elevation angle ranges between about 8° and about 12°, for example 10°, although other elevation angle values may be used in other embodiments. Furthermore, in yet other embodiments, the rear end of the support structure need not be vertically higher than the front end.

Flexible Membrane

As used herein, the term "flexible membrane" refers to any sheet-like or otherwise relatively thin layer of elastic and stretchable material which is mechanically deformed in response to the action of an applied load, for example, the force exerted by the weight of the foot received on the membrane. For simplicity, the term "flexible membrane" may, in some instances, be shortened to "membrane".

The flexible membrane can be held by and connected to the support structure using a number of fastening or anchoring mechanisms, as long as, in the intended use of the foot imaging apparatus, the membrane remains suspended from the support structure. In some embodiments, it may be possible to vary the value and/or spatial uniformity of the tension of the membrane 28 by adjusting how it is suspended from the support structure 26, for example to help achieve a semi-weight-bearing state. Furthermore, in some embodiments, the flexible membrane may be releasably affixed to the support structure. In such embodiments, the membrane can be conveniently cleaned, replaced, repaired, repositioned, tightened or loosened, or otherwise serviced.

Referring still to FIGS. 1 to 6, the flexible membrane 28 may be made of any suitable flexible material including, without limitation, polymers, plastics, thermoplastics, rubber, synthetic rubbers, elastomers, and the like. For example, in some embodiments, the flexible membrane 28 can be made of a silicone-based flexible material. The flexible membrane 28 can be made by casting, molding, extruding, thermoforming, 3D printing, or any other suitable manufacturing process or technique.

The flexible membrane 28 may have a thickness ranging from about 0.5 millimeter (mm) to about 4 mm, and particularly between about 0.8 mm and about 1.2 mm. The flexible membrane 28 may, but need not, have a uniform thickness. Also, the membrane 28 may be flat or have a preformed shape (e.g., concave or convex shape), or have a different configuration on each side thereof. As used herein, the term "preformed" is used to indicate that the flexible membrane has been subjected, prior to being affixed to the support structure, to a manufacturing process to confer to the flexible membrane a form having a predetermined size and shape and, generally, a non-flat cross-section. The term "preformed" also refers to the fact that the flexible membrane retains the intrinsic, non-flat shape conferred thereto when disposed on a flat surface. Of course, since it is made of an elastic material, the flexible membrane will nevertheless be deformed when a sufficient load is applied thereto (e.g., the weight of a foot).

In some embodiments, the membrane may have an ultimate elongation greater than 300%, for example 600%, although different values of ultimate elongation may be used in other embodiments. As known in the art, the term "ultimate elongation" refers to the percentage increase in the length of a material that occurs before the mechanical properties of the material change irreversibly (e.g., due to breakage under tension or to the onset of crystallization). Throughout the present description and unless stated otherwise, the terms "flexible", "elastic", "stretchable", "deformable", "foldable" and variants thereof can be used interchangeably to designate the ability of the membrane to be reversibly deformed under an applied load.

In the embodiment of FIGS. 1 to 6, the flexible membrane 28 includes a forefoot-receiving region 40a and a rearfoot-receiving region 40b proximate and affixed to the front end 38a and the rear end 38b of the support structure 26, respectively. It is understood that, when designating the regions of the flexible membrane 28, the terms "forefoot" and "rearfoot" refer to the fact that the forefoot and the rearfoot-receiving regions 40a, 40b are intended to receive and support the front and rear portions 42a, 42b of the foot 24, respectively. In the illustrated embodiment, because the rear end 38b of the support structure 26 is elevated relative to the front end 38a, the flexible membrane 28 is downwardly inclined toward the forefoot-receiving region 40a. The inclination angle of the suspended membrane 28 corresponds to the elevation angle of the support structure 26. In some embodiments, the support structure 26 may be configured to allow for the elevation angle of the support structure 26, and thus for the inclination angle of the membrane 28, to be adjusted over a certain angular range.

The flexible membrane 28 is configured to receive and support, alone and autonomously, the foot 24 in a semi-weight-bearing condition. Stated otherwise, during the acquisition of the topographical plantar image, the entire plantar surface of the foot 24 is supported solely by the inflatable suspended flexible membrane 28, without contact with other physical parts or components of the apparatus 20. This condition can be achieved, for example, by properly selecting the shape and the elasticity of the flexible membrane 28, and/or the way it is suspended from the support structure 26 (e.g., by elevating the rearfoot-receiving region 40b of the membrane 28 relative to the forefoot-receiving region 40a). However, it is worth reiterating that the monitoring techniques described herein can be applied for foot positioning monitoring in non-weight-bearing and full-weight-bearing conditions.

Referring still to FIGS. 1 to 6, in addition to being configured for supporting the entire plantar surface 22 of the foot 24 alone and unaided by another physical component, the flexible membrane 28 can be configured such that the rearfoot-receiving region 40b is under less tension than the forefoot-receiving region 40a. By having a higher tension in the forefoot-receiving region 40a than in the rearfoot-receiving region 40b the deformation undergone by the front portion 42a of the foot 24 can be smaller than the deformation undergone by the rear portion 42b, thus making it easier for the foot 24 to reach a semi-weight-bearing condition.

Housing

Referring still to FIGS. 1 to 6, the support structure 26 can form part of a housing 44, which generally defines the overall shape of at least an upper portion of the foot imaging apparatus 20. The housing 44 may be made of light yet sturdy and durable material including, without being limited to, molded plastic or lightweight metals or alloys. The housing 44 may also be compact and have an ergonomic shape (e.g., rounded corners and smooth surfaces) to facilitate its operation and handling.

The housing 44 can have a top wall 46, a bottom wall 48, and a sidewall 50 interconnecting the top and bottom walls 46, 48. In the illustrated embodiment, the top wall 46 is inclined at a slope angle θ relative to the bottom wall 48. The slope angle θ can correspond to the elevation angle of the support structure 26 and, thus, to the inclination angle of the flexible membrane 28. The sidewall 50 includes four wall panels, but this number may differ in other embodiments. In the illustrated embodiment, one or more transparent windows 52 may optionally be provided on the sidewall 50 to allow for the operator to better see the foot received on the flexible membrane 28 and/or to reduce the weight of the apparatus 20.

In the illustrated embodiment, the support structure 26 includes a peripheral frame 54 that encloses an opening 56 formed through the top wall 46 of the housing 44. The flexible membrane 28 is affixed to the peripheral frame 54 in a way such as to extend across and optionally hermetically seal the opening 56. When the opening 56 is hermetically sealed, the flexible membrane 28 and the housing 44 can together define and enclose an inflatable chamber 58. In the illustrated embodiment, the opening 56 generally has an ovoid shape, with a width that increases from the front end 38*a* toward the rear end 38*b* of the support structure 26. Of course, in other embodiments, the opening 56 may have another shape, for example an ellipse or a rectangle, or any other suitable regular or irregular shape. Moreover, in other embodiments, the opening 56 may have a substantially uniform width.

Inflation Unit

Referring still to FIGS. 1 to 6, the foot imaging apparatus 20 can include an inflation unit 60. The inflation unit 60 is in fluid communication with the inflatable chamber 58. The inflation unit 60 is configured to selectively supply or discharge a pressurized fluid (e.g., a gas such as air) into or from the inflatable chamber 58, using valves or other suitable actuators, to regulate an internal pressure of the inflatable chamber 58. In this manner, the inflatable chamber 58 can be selectively inflated or deflated to adjust the pressure applied to the lower side of the flexible membrane 28. In some embodiments, the pressure inside the inflatable chamber 58 can be increased up to 5 kilopascals, although other internal pressure values may be used in other embodiments. It will be understood that when the inflatable chamber 58 is pressurized, the flexible membrane 28 can form an air cushion for receiving and supporting the foot in a semi-weight-bearing condition.

3D Imager

Figure 3:
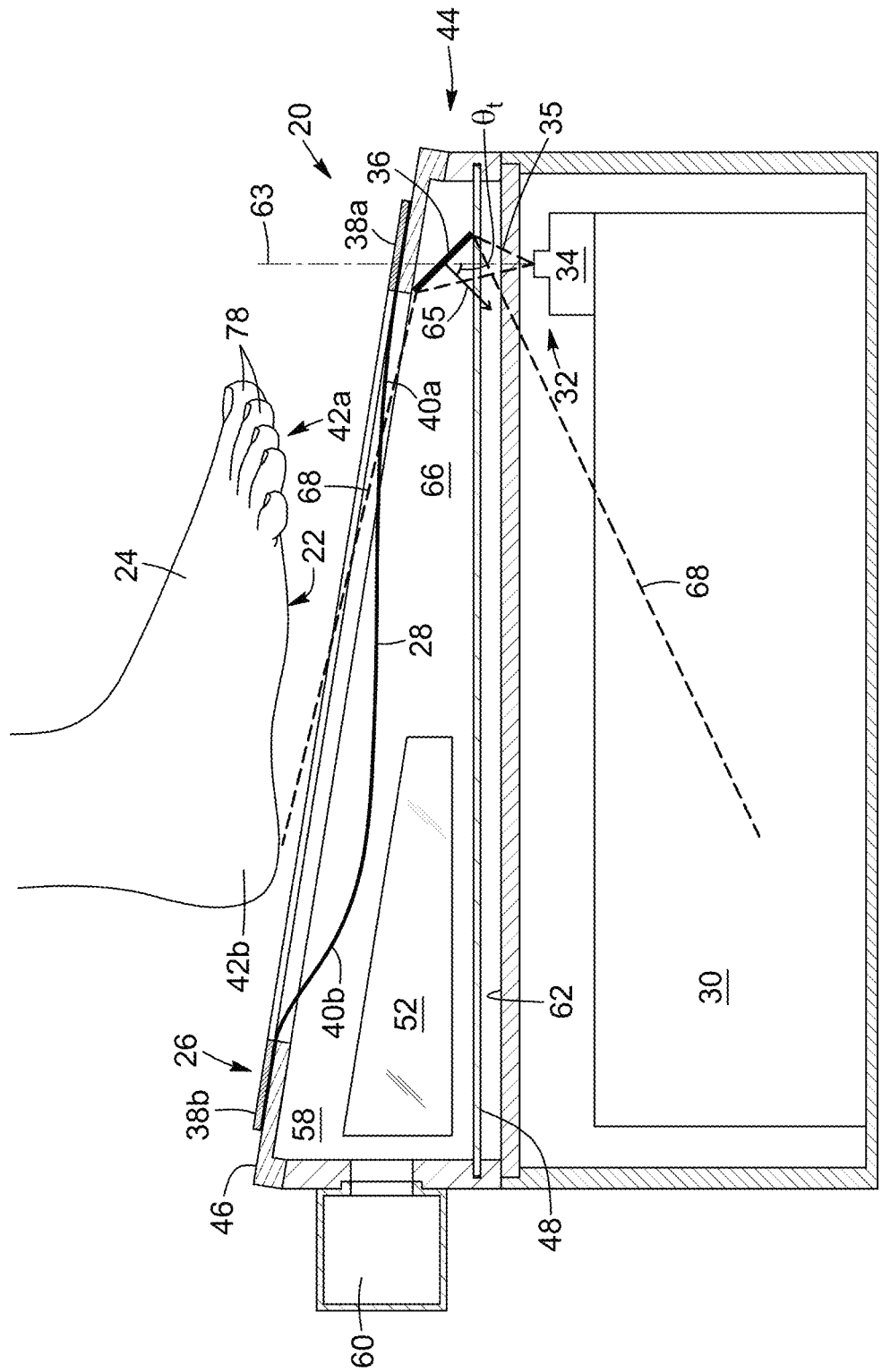
FIG. 3 is a cross-sectional side view of the apparatus of FIG. 1, taken along section line 3 and depicting a foot above the flexible membrane.
Figure 4:
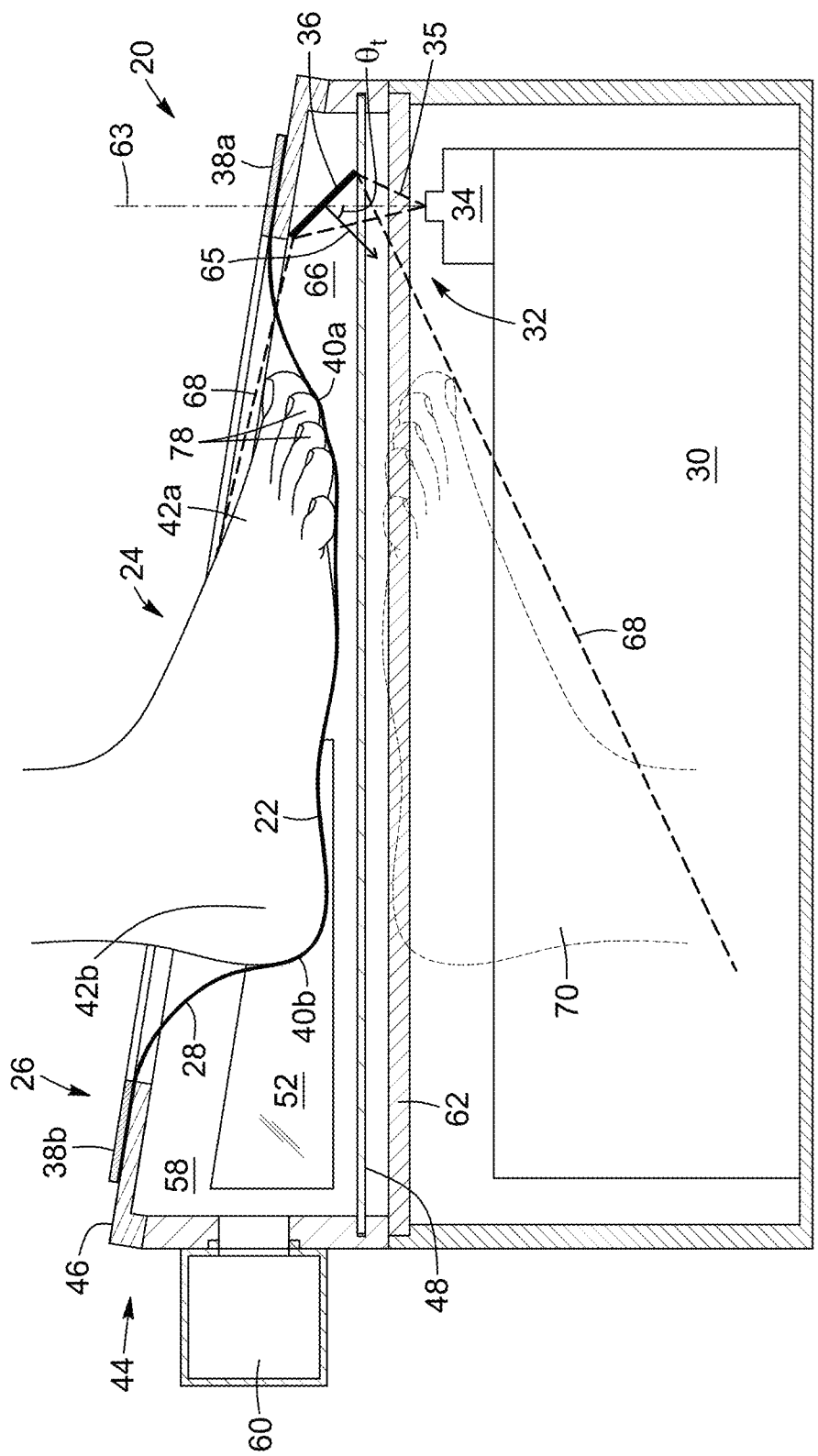
FIG. 4 is a cross-sectional side view of the apparatus of FIG. 2, taken along section line 4.
Figure 5:
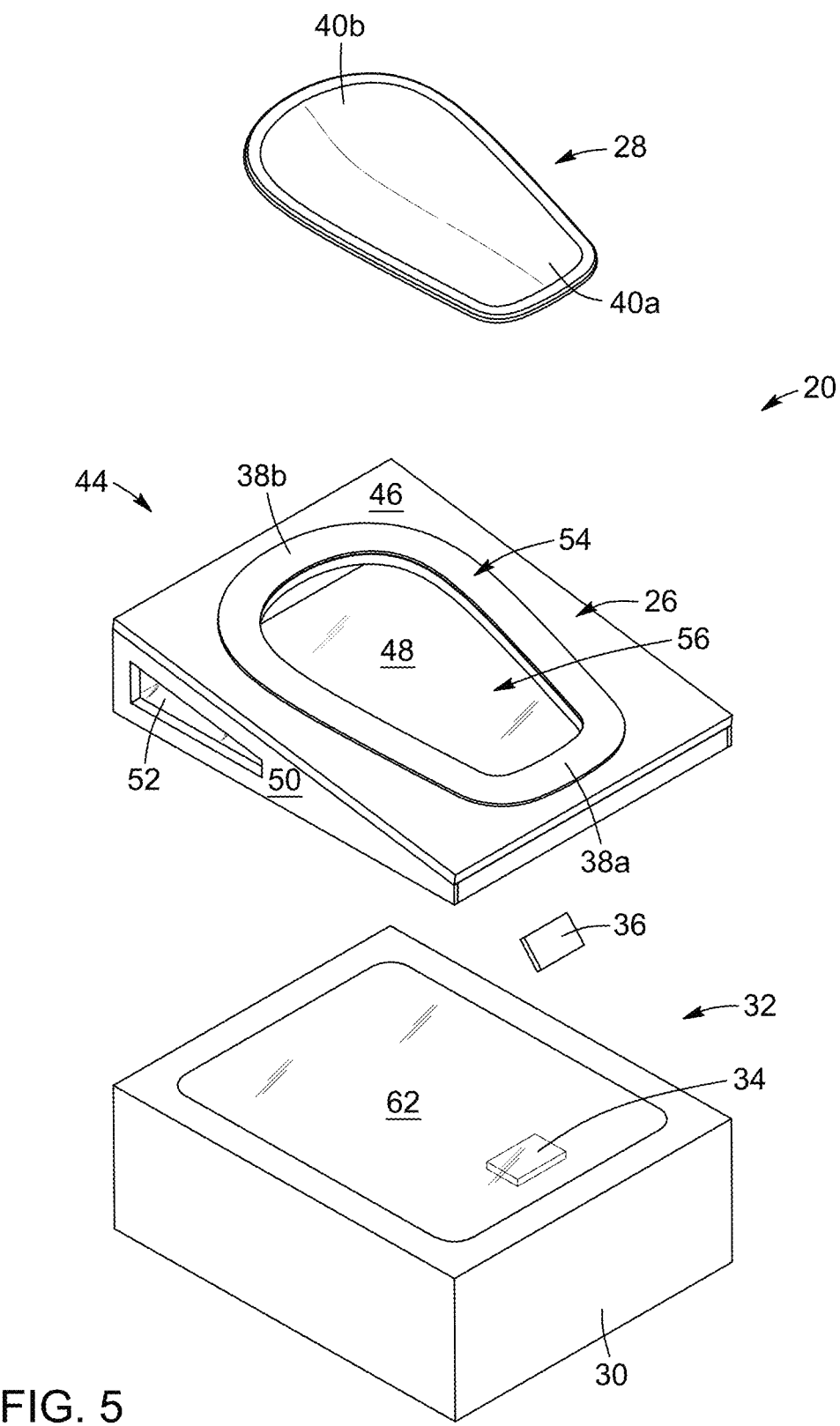
FIG. 5 is a partially exploded perspective view of the apparatus of FIG. 1.
Figure 6:
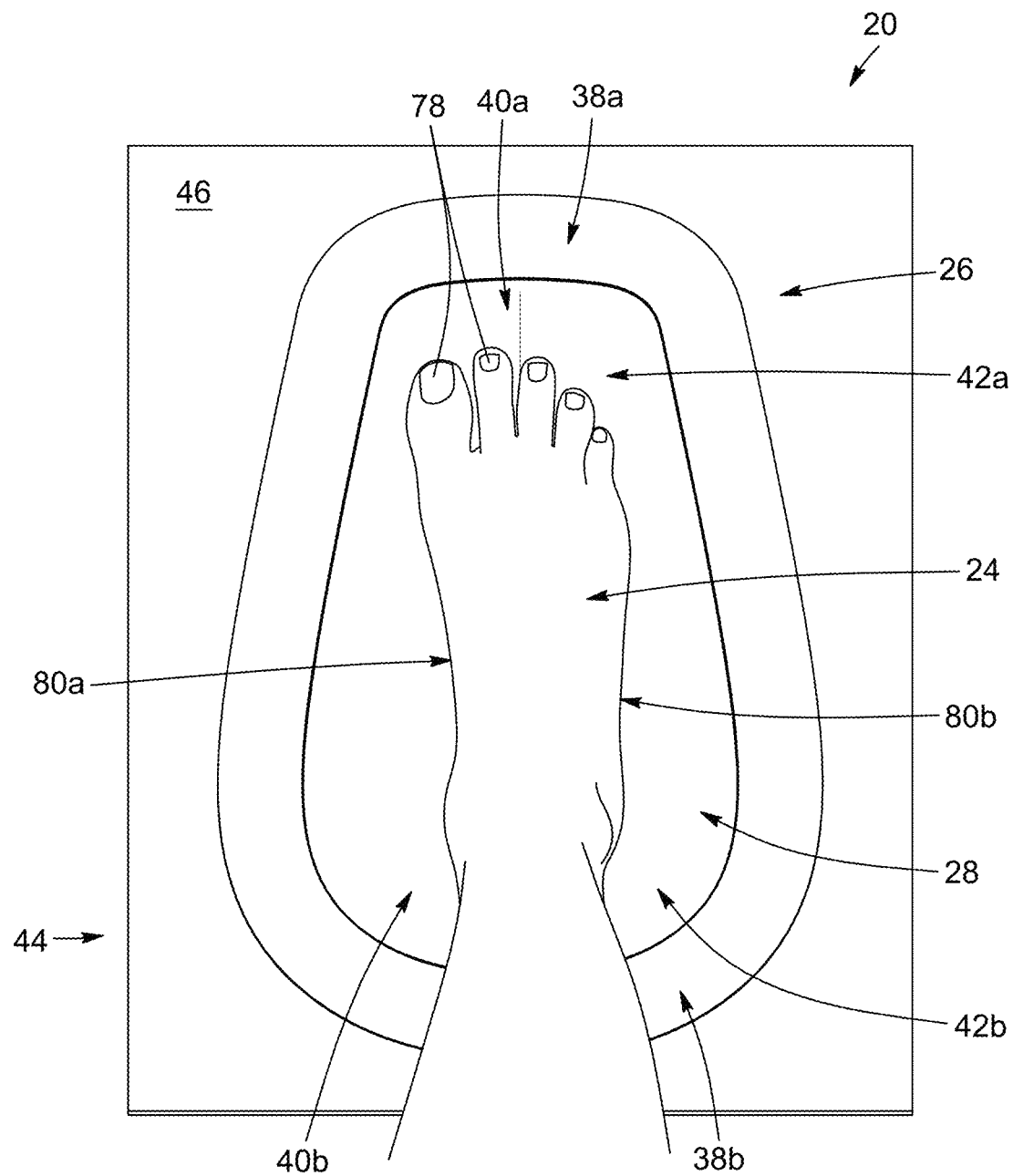
FIG. 6 is a top plan view of FIG. 1, with a foot received on the flexible membrane.

Referring still to FIGS. 1 to 6, and as better illustrated in FIG. 4, the 3D imager 30 is provided under the flexible membrane 28 to acquire the topographical image of the plantar surface 22 when the foot 24 is disposed on the flexible membrane 28. As used herein, the term "3D imager" refers broadly to any component, device or system, or combination thereof, capable of acquiring a topographical image of the plantar surface of a foot received on and supported by the flexible membrane. As mentioned above, the topographical image of the plantar surface of the foot provides a 3D model that aims to replicate the shape of the plantar surface. A topographical plantar image, or 3D plantar image, generally includes an array of data points, each designated by a spatial coordinate $Z(x, y)$, where $Z$ is the local height or elevation of the plantar surface at position $(x, y)$, generally measured from a reference plane of the 3D imager. Alternatively, the spatial coordinate of each data point of the array can be of the form $Z(x, y, z)$ or $Z(x, y, z, c)$, where $c$ represents a color associated with the point.

It should be mentioned that the terms "light", "optical" and variants thereof are intended to refer herein to electromagnetic radiation in any appropriate region of the electromagnetic spectrum, and are not a priori limited to visible light. In some embodiments, the flexible membrane may be partially or fully opaque to the electromagnetic radiation used by the 3D imager, in which case the 3D imager acquires an image of the flexible membrane deformed by the foot received thereon. However, in another embodiment, the flexible membrane may be optically transparent to the electromagnetic radiation used by the 3D imager, so that the image of the plantar surface itself is directly acquired by the 3D imager.

By way of example, in some implementations, the 3D imager 30 can be a 3D stereoscopic camera, for example using optical stereo-photogrammetry techniques. However, various conventional or specialized imaging devices, either active or passive, may be used in other embodiments, depending on performance requirements or constraints, for example in terms of field of view, spatial resolution, sensitivity, image acquisition speed, size, weight, cost, and the like. Examples of suitable types of 3D imaging devices include, without limitation, 3D laser scanners, 3D structured-light cameras, 3D time-of-flight cameras, and other imaging devices capable of acquiring 3D depth images. In some implementations, the 3D imager can include two or more 3D independent image acquisition devices whose respective outputs are combined to produce the final 3D image of the foot.

Referring more particularly to FIGS. 3 and 4, in some implementations, the housing 44 can be mounted on the 3D imager 30, with the bottom wall 48 of the housing 44 in contact or near the top surface 62 of the 3D imager 30. It will be understood that, in the illustrated embodiment, the 3D imager 30 is configured to acquire a topographical image of the plantar surface 22 as seen through both the top surface 62 of the 3D imager 30 and the bottom wall 48 of the housing 44. Therefore, both the top surface 62 of the 3D imager 30 and the bottom wall 48 of the housing 44 should be made of an optically transparent or at least partially transparent material (e.g., glass or another suitable material) on a portion thereof sufficiently large to allow a topographical image of the entire or a useful portion of the plantar foot surface to be captured by the 3D imager 30.

Figure 7:
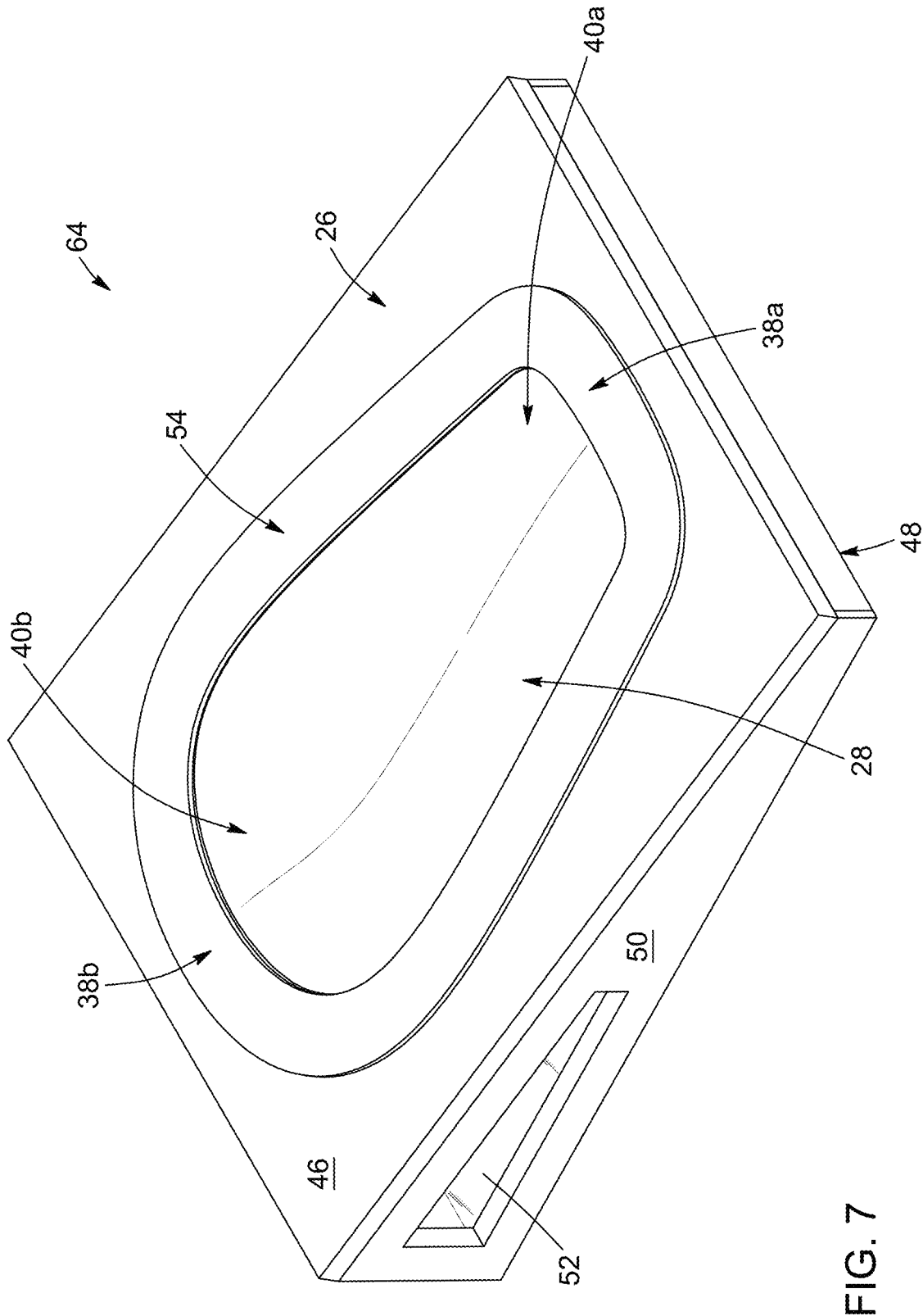
FIG. 7 is a perspective view of a membrane assembly, in accordance with another exemplary embodiment.

In the embodiment illustrated in FIGS. 1 to 6, the 3D imager 30 is releasably connected to the rest of the apparatus 20. In such a case, referring to FIG. 7, the rest of the apparatus 20, which includes the housing 44, the support structure 26 and the flexible membrane 28, can be said to define a membrane assembly or box 64. The membrane assembly 64 can be used in combination with, but manufactured and/or sold independently from, a 3D imager to provide a foot imaging apparatus.

Figure 8:
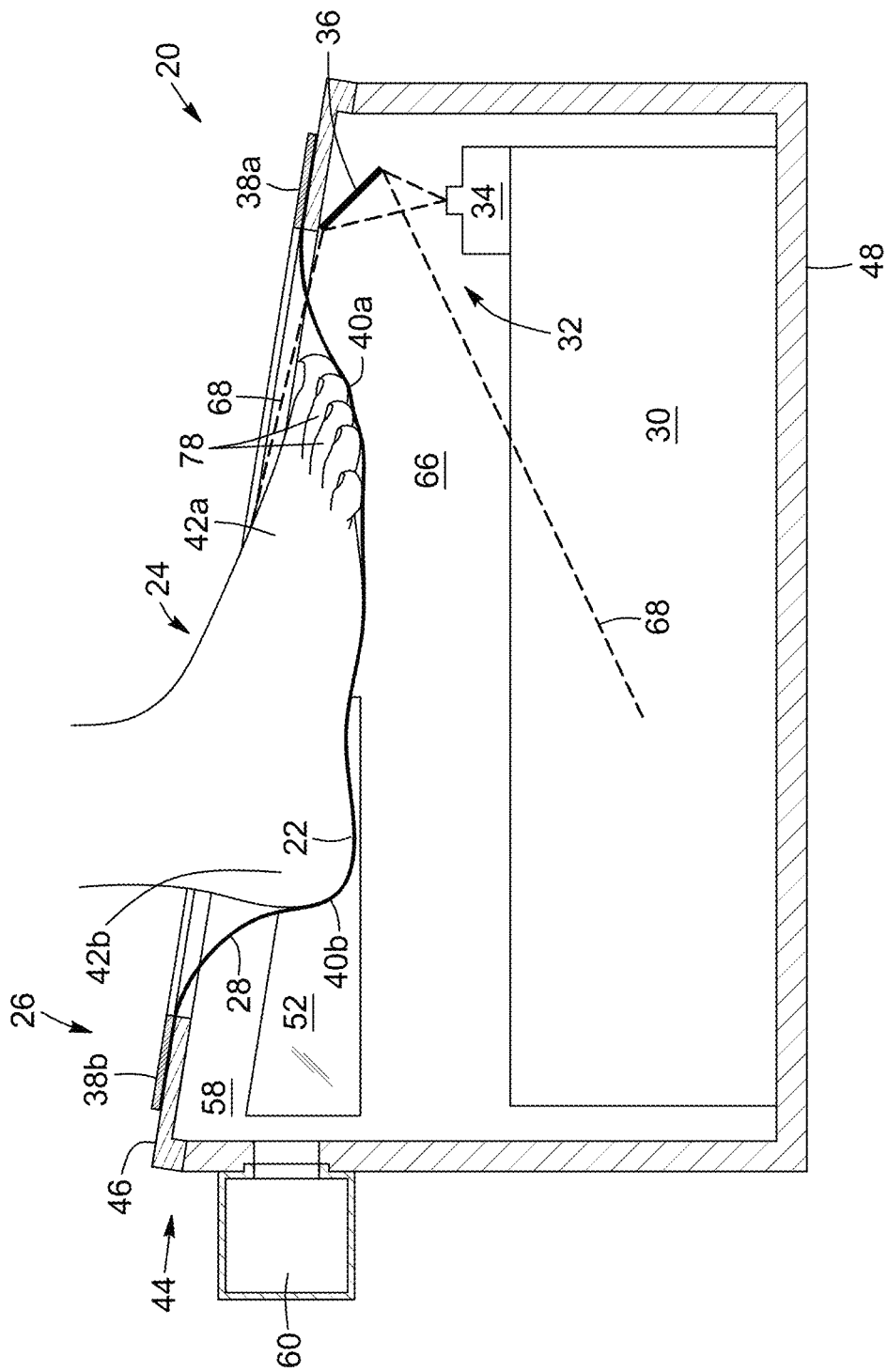
FIG. 8 is a cross-sectional side view of a foot imaging apparatus, in accordance with another exemplary embodiment.

Turning briefly to FIG. 8, in another embodiment, the 3D imager 30 may alternatively be located inside the housing 44. In such a case, the 3D imager 30 can be provided inside the inflatable chamber 58 and be provided integrally with the other components of the foot imaging apparatus 20. In such a scenario, it is possible that only one or no transparent plate be interposed between the 3D imager 30 and the flexible membrane 28.

Monitoring Unit

Referring to FIGS. 3 and 4, the foot imaging apparatus 20 also includes a monitoring unit 32 for monitoring a monitoring region 66 in order to evaluate a positioning of the foot on the flexible membrane. The provision of the monitoring unit 32 can allow the foot's correct positioning to be assessed in view of the imaging process. The monitoring unit 32 is configured to acquire or capture a monitoring image indicative of the positioning of the foot 24 received on the flexible membrane 28. In other words, the monitoring image contains information about the positioning of the foot 22 on the flexible membrane 28.

As mentioned above, in some implementations, imaging a foot in a semi-weight-bearing state can be desirable or even necessary. This is due, at least partly, to the fact that the amount of soft tissue deformation under semi-weight bearing can be controlled more accurately and be more representative of the natural physiological deformation of the foot under the weight of the body. Non-limiting techniques for achieving 3D foot imaging under semi-weight bearing are disclosed in International PCT Application No. PCT/CA2015/050453, filed May 20, 2015 and published Nov. 26, 2015 as WO 2015/176183, the contents of which are incorporated herein by reference in their entirety.

By way of example, achieving a semi-weight-bearing state can involve implementing one or more of the following:

acquiring the 3D plantar image with the entire plantar surface of the foot received on and supported solely by a flexible and inflatable membrane suspended from a support structure, without contact with an underlying reference plane;

configuring the support structure such that the width of the opening of the support structure across which the membrane is supported increases from the front end toward the rear end of the support structure;

configuring the flexible membrane such that the rear-foot receiving region of the membrane is connected higher on the support structure than the forefoot-receiving region to compensate for the force exerted by the foot on the rearfoot-receiving region of the membrane being greater than that exerted on the forefoot-receiving region, due to the additional downwardly directed force generally applied by the operator on the patient's knee;

configuring the flexible membrane such that the rear-foot receiving region of the membrane is under less tension than the forefoot-receiving region, which can involve:

(i) adjusting the physical properties of the flexible membrane itself, for example by preforming the membrane so that its upper, foot-receiving surface includes a concave recessed area in the rearfoot-receiving region, and/or by providing the membrane with a thickness greater in the forefoot-receiving region than in the rearfoot-receiving region; and/or (ii) adjusting the way the membrane is suspended from the support structure, for example by controlling the uniformity of the tension in the membrane affixed to the support structure.

As also mentioned above, achieving semi-weight bearing in 3D foot imaging using a suspended flexible membrane can be challenging, because the foot, notably the forefoot, is typically not readily visible to the operator during the image capture process. As will now be described, the present techniques provide a monitoring unit that aims to address or at least alleviate this challenge.

Referring to FIGS. 3 and 4, in some embodiments, the monitoring unit 32 can include a camera 34 having a field of view 35, and at least one light deflector 36 arranged to deflect light from the monitored region 66 into the field of view 35 of the camera 34. The camera 34 acquires a monitoring image of the monitored region 66 after deflection by the at least one light deflector 36. Information about the positioning of the foot 24 on the membrane 28 can be obtained from the monitoring image thus acquired. In the illustrated embodiment, the monitoring unit 32 includes a single light deflector 36. However, other embodiments can include more than one light deflector positioned and arranged to successively redirect light from the monitored region to the camera. The field of view 35 of the camera 34 encompasses at least partly, and in some cases, entirely, the light deflector 36. It may be advantageous, in some implementations, that the field of view of the camera 34 be filled as much as possible by the light deflector 36, since generally no valuable information about the positioning of the foot on the membrane 28 can be retrieved from regions of the image that are not viewed through the light deflector 36.

As used herein, the term "camera" refers broadly to any device or combination of devices capable of capturing and outputting images of a scene, either as still images or as a video stream. Depending on the application or use, different types of cameras can be used including, without limitation, complementary metal-oxide-semiconductor (CMOS) or charge-coupled device (CCD) based cameras. The camera can employ a static or rolling type shutter capable of producing both still images and video streams with frame rates varying, without limitation, from 10 to 240 frames per second, for example 30 frames per second. In some embodiments, the camera can be a high-resolution digital camera, although lower resolution cameras (e.g., 0.3 megapixels) and/or non-digital devices may be used in other embodiments. The camera can be sensitive to the visible and/or the infrared wavelength ranges, although other wavelength ranges are not excluded a priori.

The camera can include an image sensor and collecting optics adapted to collect light from the monitored region and to direct the collected light onto the image sensor. The collecting optics may include lenses, mirrors, filters and any other suitable reflective, refractive and/or diffractive optical components. The image sensor can be a device made up of a plurality of pixels capable to detect electromagnetic radiation incident thereonto and to generate an image from the detected radiation. The pixels may be arranged in a two-dimensional array. By way of example, the image sensor may be embodied by a CMOS or a CCD image sensor, but other types of sensor arrays (e.g., charge injection devices or photodiode arrays) could alternatively be used.

As used herein, the term "light deflector" is intended to refer to an optical element or a combination of optical elements which can redirect, at least partly, the optical path of light incident thereonto, for example an image of an object. In the present techniques, each light deflector is arranged relative to the monitored region and the camera to intercept light originating from the monitored region (or from another light deflector when the monitoring unit includes more than one light deflector) and to deflect the intercepted light toward the camera (or toward another light deflector). Each light deflector can be embodied by a reflecting, a refracting or a diffracting element, or by a combination thereof. Non-limiting examples of light deflectors include plane and curved mirrors, beam splitters, prisms, filters, diffraction gratings and holographic elements. By way of example, the light deflectors 36 illustrated in the Figures are light reflectors embodied by plane mirrors lying at least partly in the field of view 35 of the camera 34 and preferably having a high reflectivity in the visible and/or infrared ranges. Also by way of example, in one non-limiting embodiment a plane mirror 40 mm wide by 15 mm high can be used.

The provision of one or more light deflectors can be required or beneficial in some implementations where the configuration and design of the foot imaging apparatus can make it difficult, or even impossible, to accommodate a camera in front of the forefoot-receiving region of the membrane, due to a lack of available space or room and/or the fact that the camera would be too close to the forefoot-receiving region to get adequate focus or view of the forefoot. In some instances, it may also be undesirable to place a camera inside the membrane assembly, as this would generally entail data transfer via additional wired cables, data connectors or other similar components or techniques, thus possibly complicating the design of the apparatus. In some implementations, these issues can be overcome or at least alleviated by placing the camera further away from the flexible membrane and by providing one or more light deflectors to redirect light from the monitored region onto the field of view of the camera for capture thereby. For example, in some implementations, the camera can be accommodated in the 3D imager, where suitable data connectors are generally more readily available. In some implementations, the monitoring unit can include a camera but no light deflector (see, e.g., FIG. 10A).

The provision of one or more light deflectors will generally modify, enhance, redirect, extend or otherwise modify the field of view of the camera. By way of example, in the embodiment of FIGS. 3 and 4, the light deflector 36 redirects the field of view 35 of the camera 34 toward the monitored region 66, which otherwise would not be visible within the field of view 35 of the camera 34 alone. In this exemplary embodiment, the light deflector 36 is arranged to deflect light from the monitored region 66 into the field of view 35 of the camera 34 for capture by the camera 34 as a monitoring image. The monitoring image contains image information relating to the foot positioning. The image information can be analyzed to allow a determination of whether the foot 24 is correctly positioned on the membrane 28. This determination is possible even though neither the foot 24 nor a reflection thereof off a reflective surface (depicted by phantom lines in the Figures) is directly visible in the field of view 35 of the camera 34 alone. The field of view of a camera as modified by at least one light deflector will be referred to herein as the "field of view of the monitoring unit". In the Figures, the field of view of the monitoring unit 32 will be designated by reference numeral 68.

Referring still to FIGS. 3 and 4, the camera 34 is located inside the 3D imager 30, near the top surface 62. The field of view 35 of the camera 34 is defined by an axis 63 that points vertically upward. As used herein, the terms "vertical" or "vertically" refer to a direction extending substantially along (i.e., "vertically downward") or opposite (i.e., "vertically upward") to the direction of gravity, while the terms "horizontal" or "horizontally" refer to a plane or a direction extending substantially perpendicularly to the direction of the gravity. The field of view 35 of the camera 34 encompasses the light deflector 36 located inside the housing 44 of the membrane assembly 64, directly in front of the forefoot-receiving region 40a of the membrane 28. The camera 34 is therefore configured to acquire the monitoring image through the bottom wall 48 of the housing and the top surface 62 of the 3D imager 30. In the illustrated embodiment, the light deflector 36 is a plane mirror having a surface normal 65 oriented at a tilt angle $\theta_t$ with respect to the axis 63 of the field of view 35 of the camera 34 to redirect the field of view 35 of the camera 34 to provide the camera 34 with an adequate view of the front portion 42a of the foot 24. In some embodiments, the tilt angle $\theta_t$ can range from 30° to 60°. For example, in some of these embodiments, the tilt angle $\theta_t$ can be equal to 45°. However, any appropriate tilt angle value can be used in other embodiments. The horizontal reference plane is generally parallel to the top surface 62 of the 3D imager 30 and the bottom wall 48 of the housing 44. Other orientations for the light deflector 36 can be used in other implementations.

The camera and the at least one light deflector are generally arranged with respect to the flexible membrane such that the monitoring image provides at least one of a view of the flexible membrane with the foot thereon and a view of a reflection off an underlying reflective surface of the flexible membrane with the foot thereon. By way of example, in FIGS. 3 and 4, the field of view 68 of the monitoring unit 32 (i.e., the field of view 35 of the camera 34 as modified by the light deflector 36) is sized and oriented to acquire at the same time both an image of the membrane 28 itself with the foot 24 received thereon and the image of its reflection 70 off the bottom wall 48 of the housing 44. However, in other implementations, either the image of the membrane itself or the image of its reflection may be absent from or partially visible in the monitoring image acquired by the monitoring unit.

The implementation of the monitoring unit 32 illustrated in FIGS. 3 and 4 is provided by way of example only, and that various other configurations may be used for the monitoring unit 32 in other embodiments of the foot imaging apparatus 20. Non-limiting examples of alternative implementations of the monitoring unit 32 are discussed below.

Figure 9A:
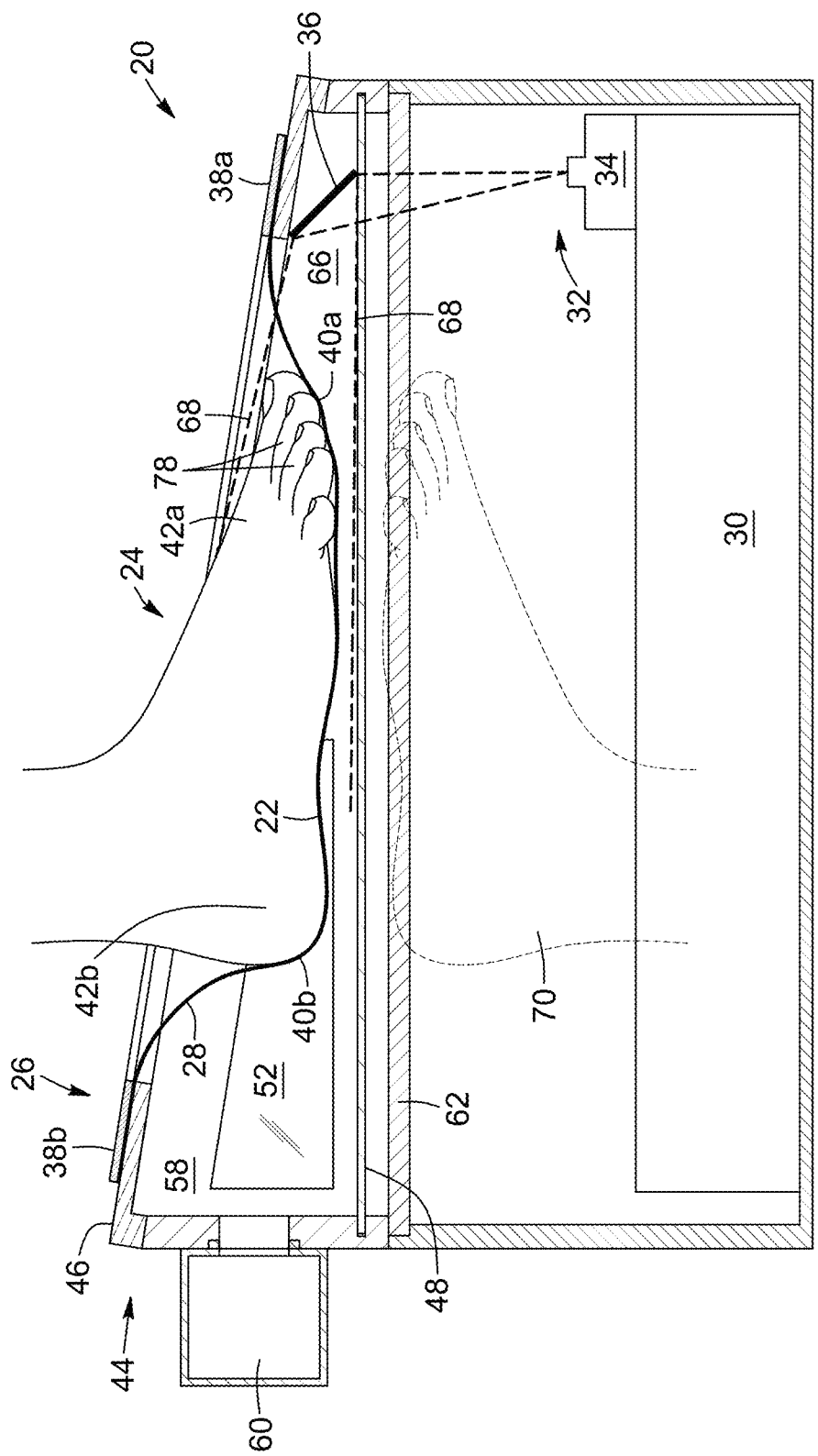
FIG. 9A is a cross-sectional side view of a foot imaging apparatus, in accordance with another exemplary embodiment.
Figure 9B:
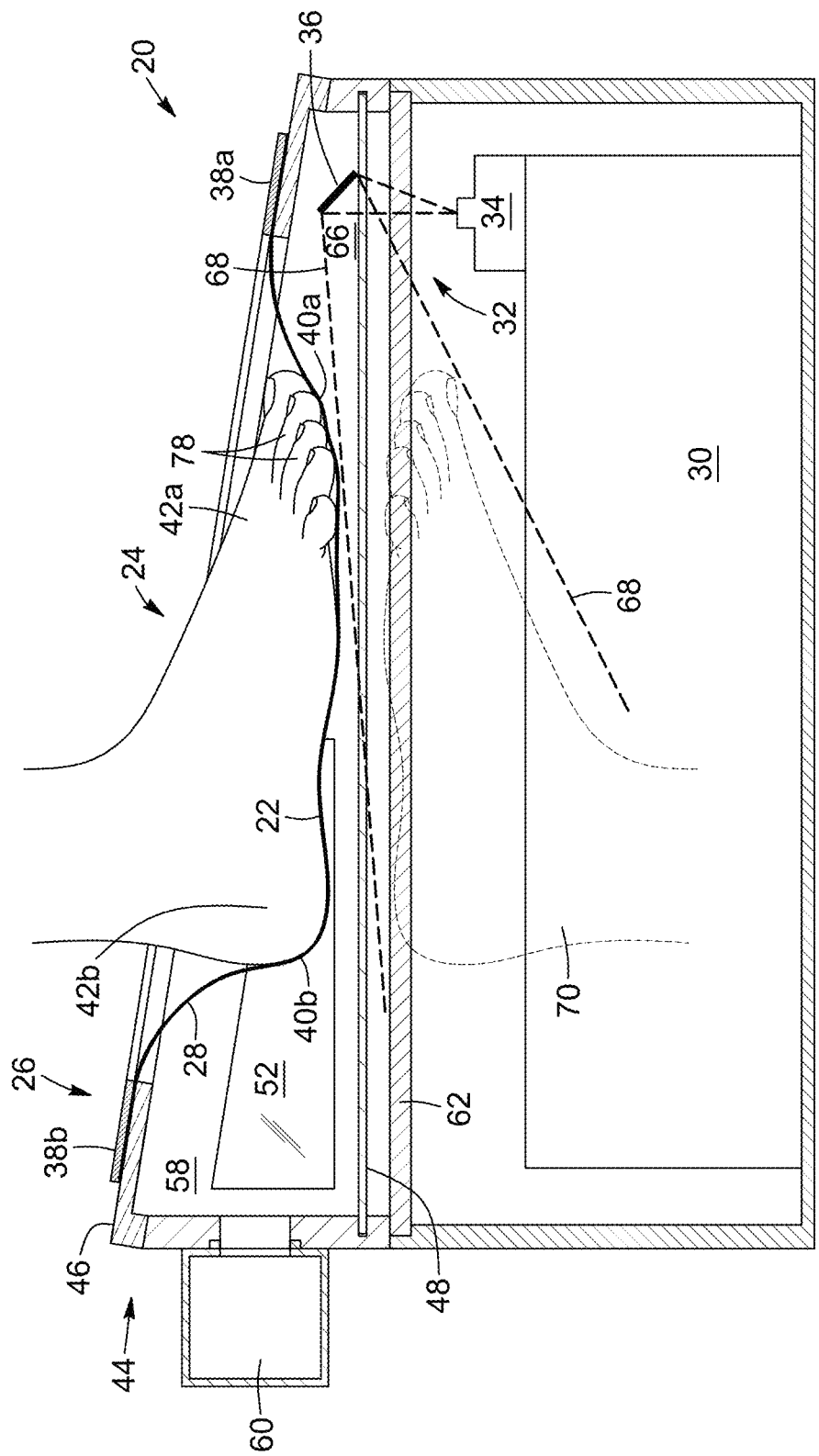
FIG. 9B is a cross-sectional side view of a foot imaging apparatus, in accordance with another exemplary embodiment.

Referring to FIGS. 9A and 9B, in some implementations, the field of view 68 of the monitoring unit 32 may be sized and oriented to capture a monitoring image that contains a view of either, but not both, of the flexible membrane 28 and a reflection 70 thereof off an underlying reflective surface. More specifically, in FIG. 9A, the monitoring image acquired by the camera 34 provides a view of only the flexible membrane 28 with the foot 24 thereon, while in FIG. 9B, the monitoring image acquired by the camera 34 provides a view of only the reflection 70 of the flexible membrane 28 with the foot 24 thereon, where the underlying reflective surface is embodied by the bottom wall 48 of the housing 44.

Figure 10A:
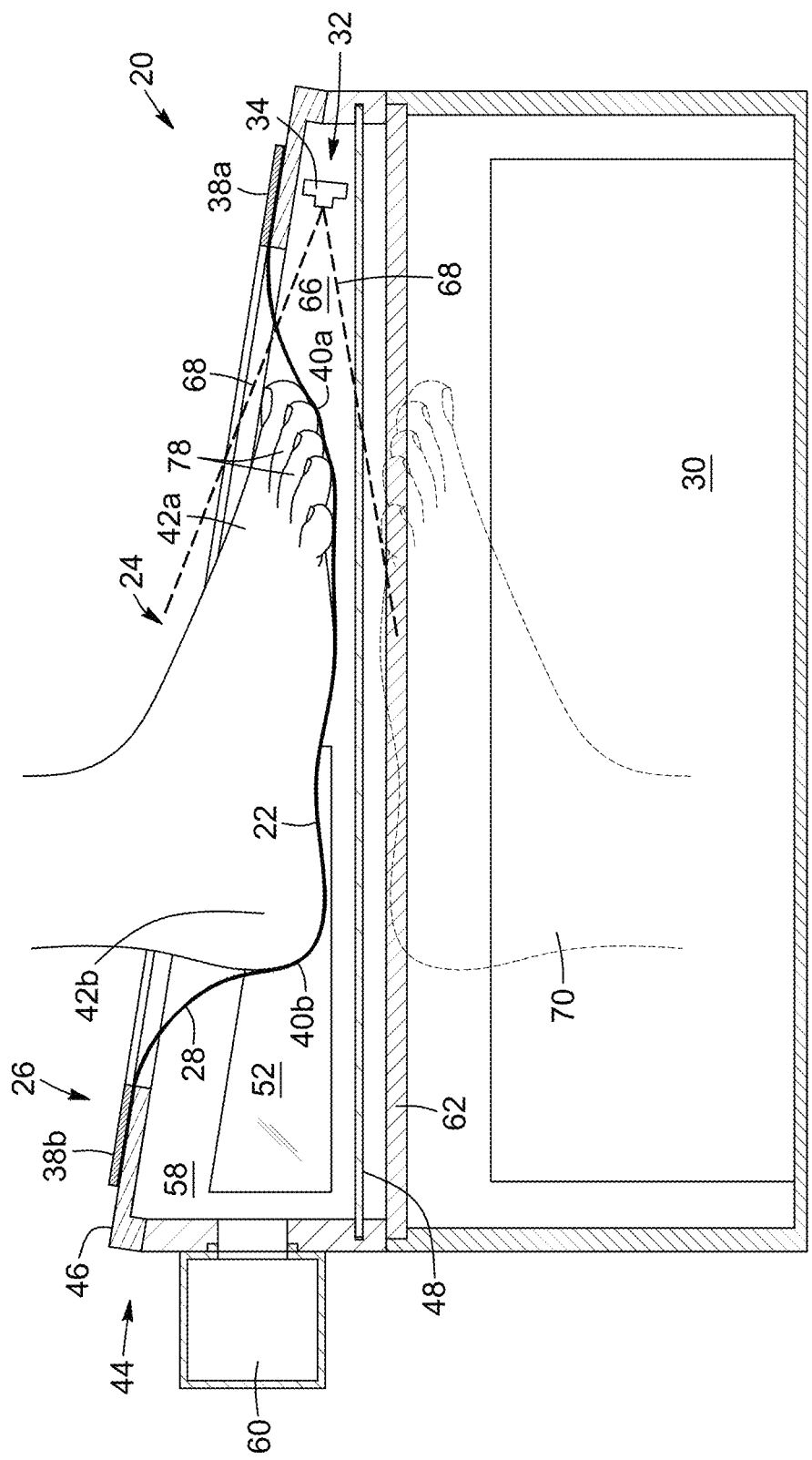
FIG. 10A is a cross-sectional side view of a foot imaging apparatus, in accordance with another exemplary embodiment.
Figure 10B:
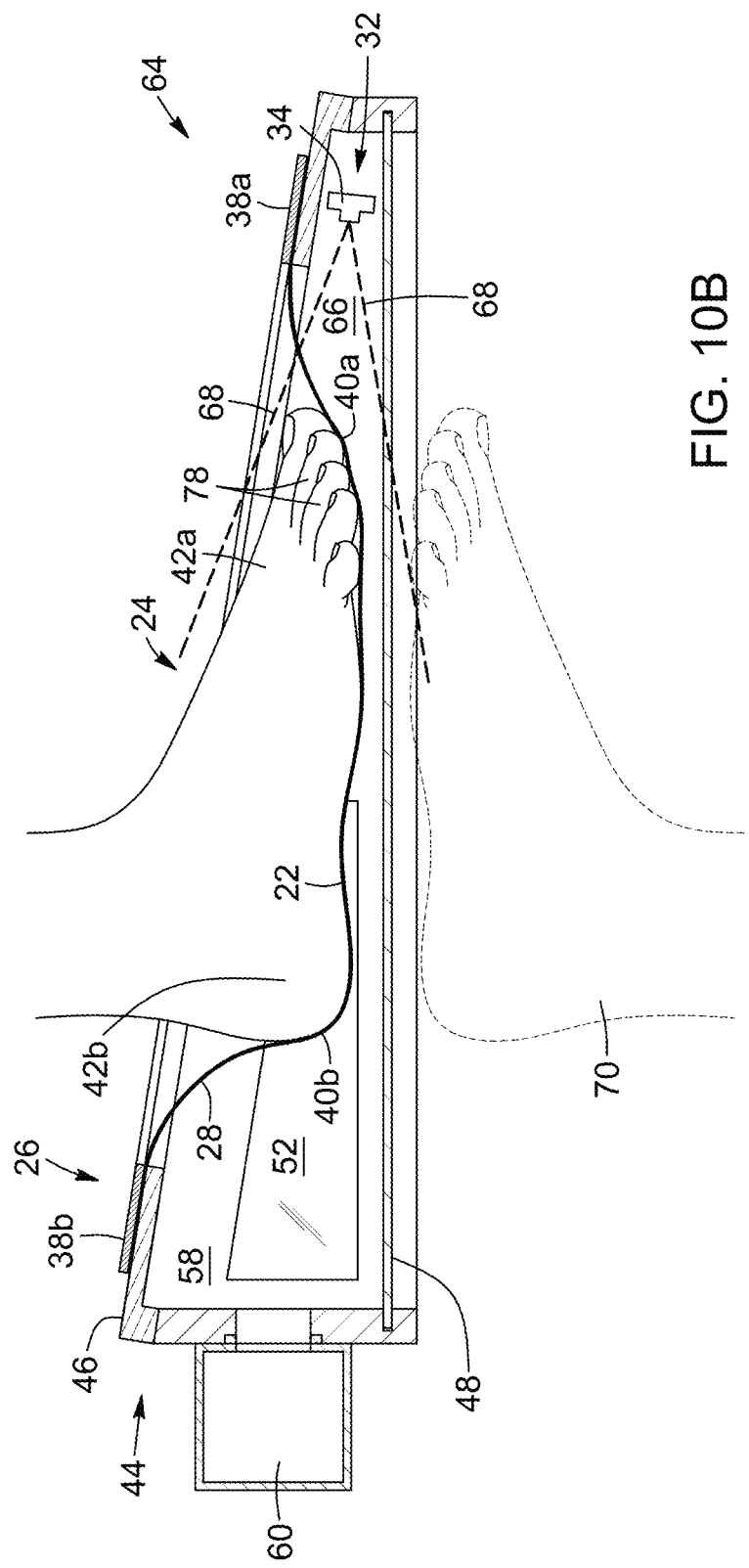
FIG. 10B is a cross-sectional side view of the membrane assembly of the foot imaging apparatus of FIG. 10A.

Referring now to FIG. 10A, in some implementations, the monitoring unit 32 can include a camera 34 but no light deflector. In such a case, the field of view 68 of the monitoring unit 32 coincides with the field of view of the camera 34. In FIG. 10A, the camera 34 is positioned so that its field of view encompasses at least part of the forefoot-receiving region 40a of the membrane 28 when the foot 24 is received thereon, as well as at least part of the top surface 62 of the 3D imager 30 and of the bottom wall 48 of the housing 44, both of which in this embodiment are embodied by flat, optically transparent plates (e.g., glass plates). It is noted that in the embodiment of FIG. 10A, a membrane assembly 64 including the camera 34 thereinside can be manufactured and/or sold independently from the 3D imager (see FIG. 10B), but used in combination therewith to form the foot imaging apparatus 20. Also, as mentioned above, in other implementations, the camera may be configured to capture an image containing either, but not both, of the membrane and a reflection thereof.

Figure 11:
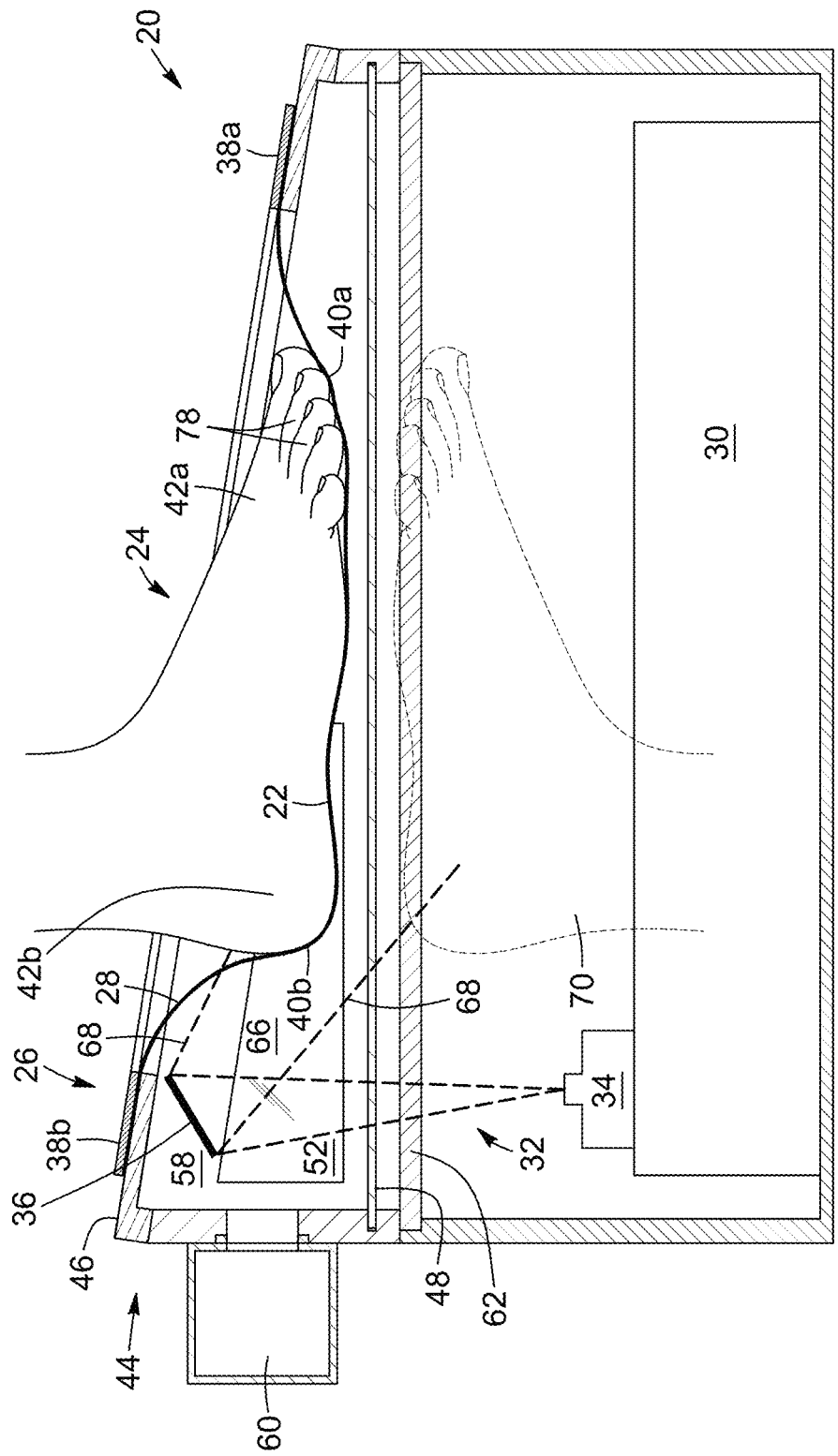
FIG. 11 is a cross-sectional side view of a foot imaging apparatus, in accordance with another exemplary embodiment.

As mentioned, in some implementations, it may be desirable or beneficial that the monitoring unit be arranged and configured to monitor the front portion of the foot, notably under semi-weight bearing (see, e.g., FIGS. 3, 4, 9A, 9B, 10A and 10B described above). In such a case, the camera 34 and the at least one light deflector 36 are arranged with respect to the flexible membrane 28 such that the monitoring image provides a front elevation view of the foot 24 received on the flexible membrane 28 (see, e.g., FIGS. 2, 14A, 14B, 15A and 15B). However, in other implementations, one or more other regions of the foot may alternatively or additionally be monitored by the monitoring unit 32. By way of example only, FIG. 11 illustrates an embodiment of a foot imaging apparatus 20 in which the monitoring unit 32 includes a camera 34 and a light deflector 36 which together are arranged and configured for imaging the rear portion 42b of the foot 24 received on the membrane 28. In such a case, the camera 34 and the at least one light deflector 36 are arranged with respect to the flexible membrane 28 such that the monitoring image provides a rear elevation view of the foot 24 received on the flexible membrane 28 (see, e.g., FIG. 17). In yet other implementations, the monitoring unit may be configured to image the underside of the membrane 28 from any suitable viewpoint, for example from the inner and/or outer side thereof.

Figure 19:
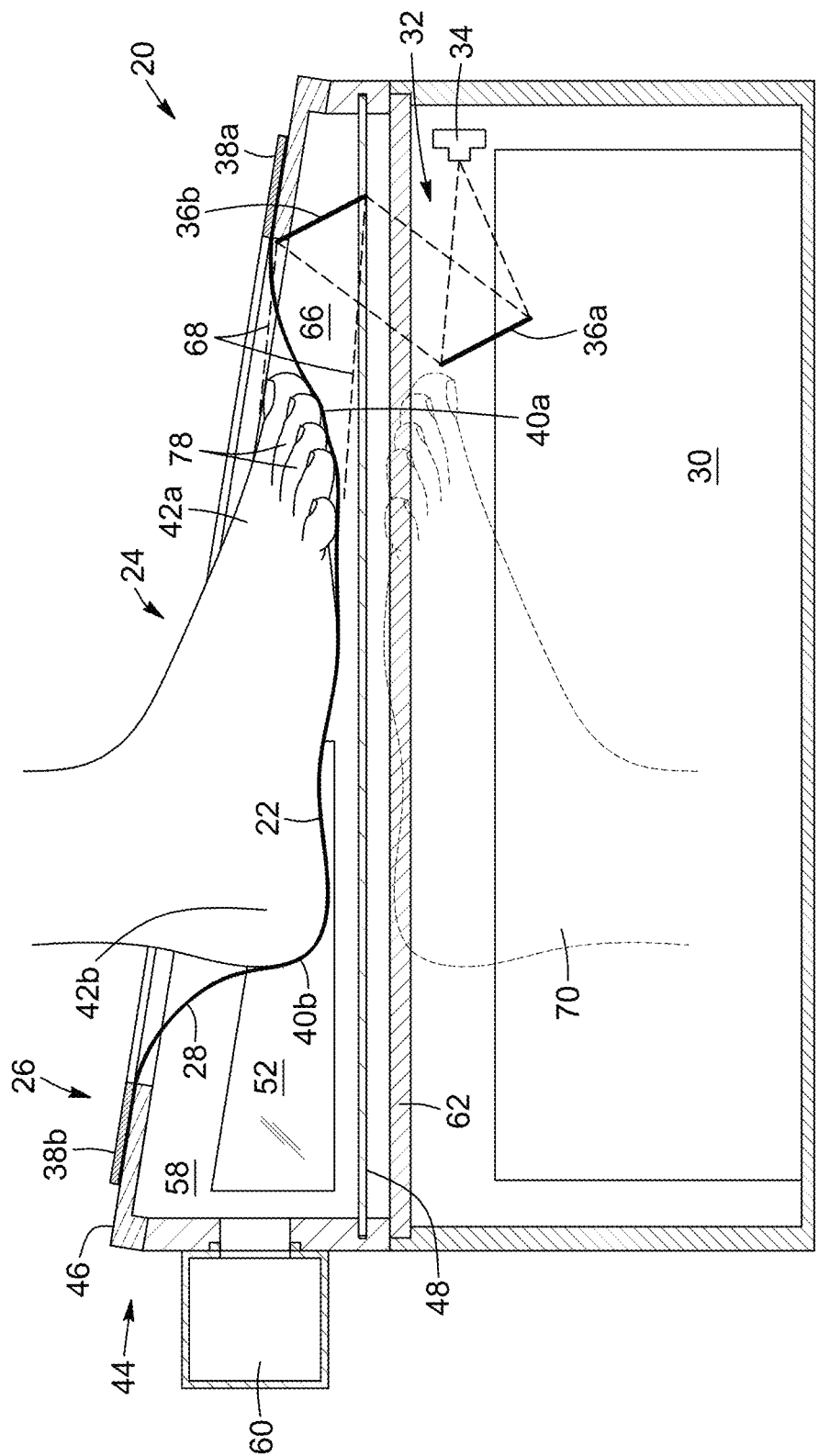
FIG. 19 is a cross-sectional side view of a foot imaging apparatus, in accordance with another exemplary embodiment.

Turning to FIG. 19, in some implementations, the monitoring unit 32 of the foot imaging apparatus 20 may have a plurality of light deflectors 36a, 36b successively deflecting light along an optical path ending at the camera 34. For example, two light deflectors 36a, 36b, embodied by two plane mirrors, are provided in the embodiment of FIG. 19 to successively redirect the field of view of the camera 34 toward the monitored region 66. Depending on the application or use, the plurality of light deflectors may be different from or identical to one another. By way of example, in a non-limiting embodiment, one or more of the light deflectors may be embodied by mirrors and one or more of the light deflectors may be embodied by prisms.

Figure 12:
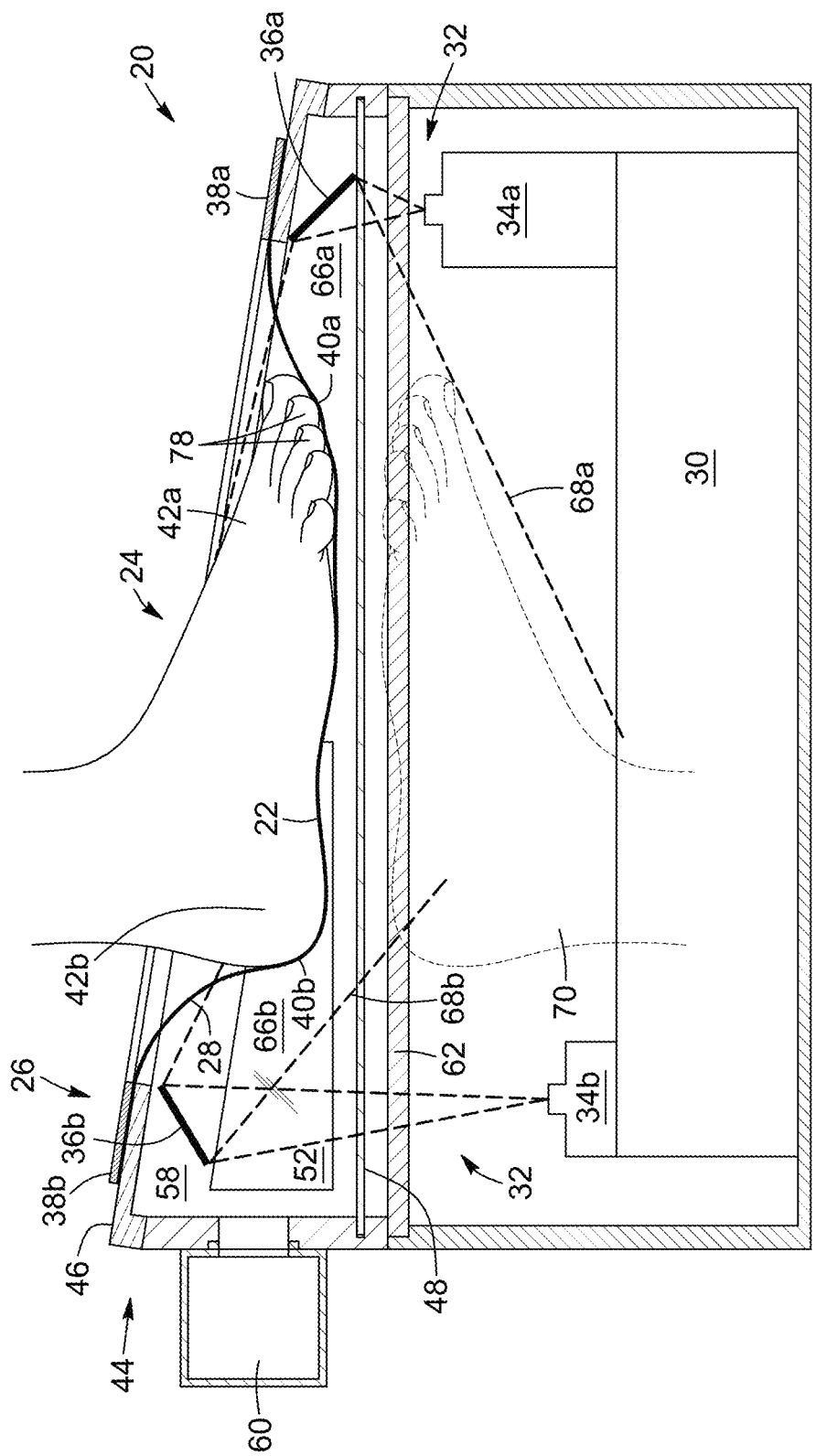
FIG. 12 is a cross-sectional side view of a foot imaging apparatus, in accordance with another exemplary embodiment.

Referring now to FIG. 12, in some implementations, the monitoring unit 32 may be provided with more than one camera 34, each of which having no, one or more than one light deflectors 36 optically coupled thereto. By way of example, in FIG. 12, the monitoring unit includes first and second cameras 34a, 34b and associated first and second light deflectors 36a, 36b. The first camera 34a and the first light deflector 36a together define a first field of view 68a encompassing a first monitored region 66a, whereas the second camera 34b and the second light deflector 36b together define a second field of view 68b encompassing a second monitored region 66b. In FIG. 12, the first camera 34a and first light deflector 36a are configured to monitor foot positioning from a viewpoint located in front of and looking longitudinally toward the front portion 42a of the foot 24 received on the membrane 28. The monitoring image acquired by the first camera 34a therefore provides a front elevation view of the foot 24 received on the flexible membrane 28 (see, e.g., FIGS. 2, 14A, 14B, 15A and 15B). Meanwhile, the second camera 34b and the second light deflector 36b are configured to monitor foot positioning from a viewpoint located behind of and looking longitudinally toward the rear portion 42b of the foot 24 received on the membrane 28. The monitoring image acquired by the second camera 34b therefore provides a rear elevation view of the foot 24 received on the flexible membrane 28 (see, e.g., FIG. 17). In implementations, some of or all the cameras may be temporally synchronized. In some implementations, some of or all the cameras may have overlapping fields of view (modified or not by one or more light deflectors).

Figure 13A:
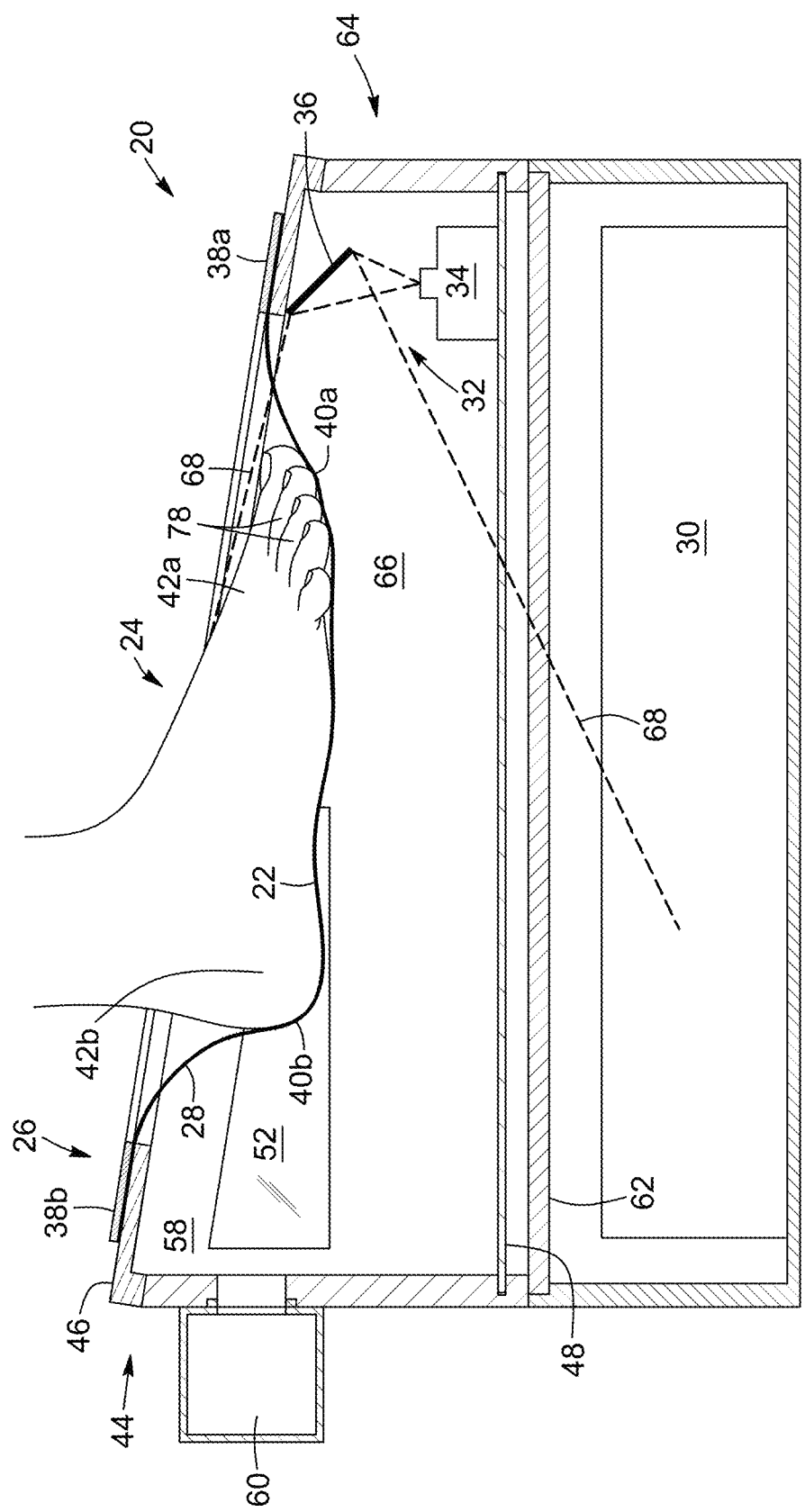
FIG. 13A is a cross-sectional side view of a foot imaging apparatus, in accordance with another exemplary embodiment.
Figure 13B:
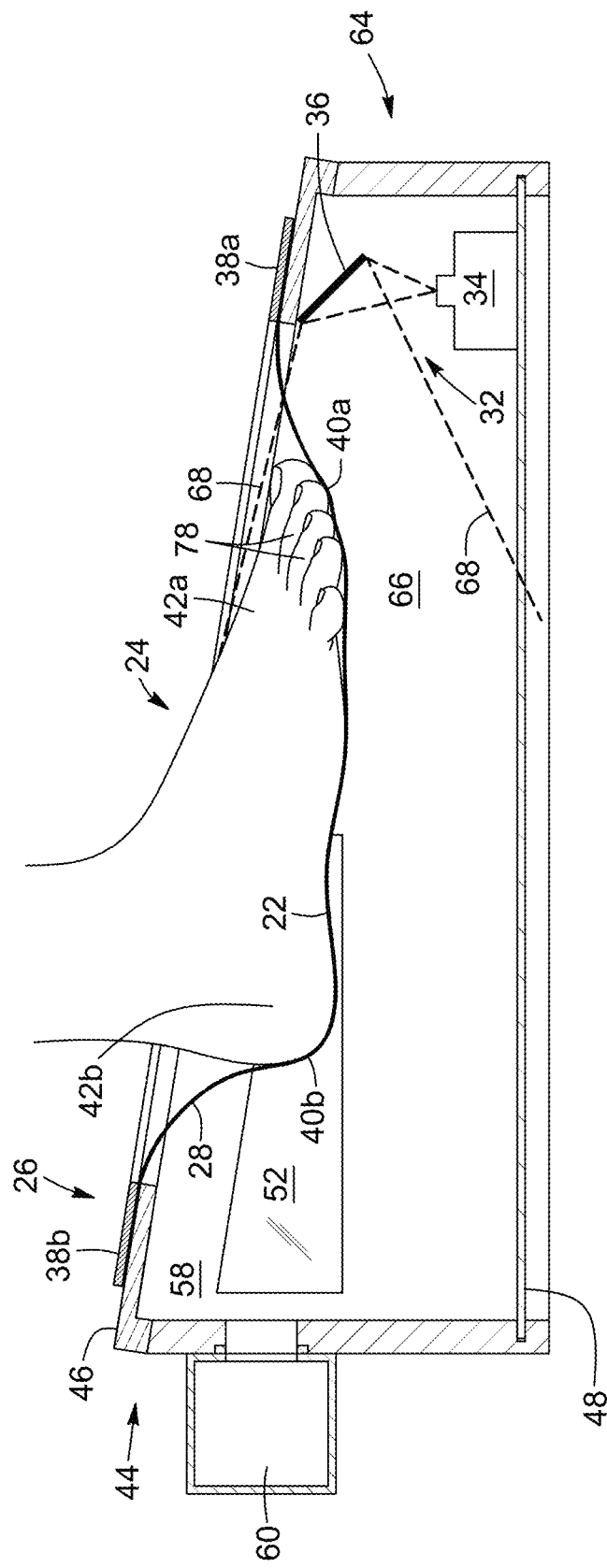
FIG. 13B is a cross-sectional side view of the membrane assembly of the foot imaging apparatus of FIG. 13A.

Turning to FIG. 13A, in some implementations, the monitoring unit 32 may be provided entirely inside the membrane assembly 64. Indeed, as illustrated in FIG. 13A, both the camera 34 and the light deflector 36 are inside the membrane assembly 64. As mentioned above regarding FIGS. 10A and 10B, in such a case, a membrane assembly 64 containing a monitoring unit 32 thereinside (e.g., including a camera and a light deflector) can be manufactured and/or sold independently from the 3D imager, but used in combination therewith to form a foot imaging apparatus (see FIG. 13B). However, in other embodiments, the monitoring unit may be provided entirely or partly inside the 3D imager. By way of example, in some embodiments, the camera can be located inside the 3D imager and the at least one deflector can be located inside the membrane assembly. In yet other embodiments, the camera can be located inside the 3D imager and the at least one deflector can include a plurality of light deflectors, at least one of which being located inside the membrane assembly and at least one of which being located inside the 3D imager.

In some implementations, the position, orientation, field of view, zoom level and the like of each camera and light deflector of the monitoring unit can be varied, sometimes in real-time, to observe the foot on the membrane from different viewpoints Visual Display Device Returning to FIGS. 1 and 2, the foot imaging apparatus 20 can include or be connectable to a visual display device 72 including a visual display screen 74, for example a flat screen or a projector projecting images on a wall or screen. The visual display device 72 is coupled to the camera 34 of the monitoring unit 32. The visual display device 72 receives and displays the monitoring image captured by the camera 34 and indicative of the positioning of the foot 24 on the membrane 28. Depending on the application or use, data communication and transfer between the camera 34 and the visual display device 72 may be wired, wireless or a combination thereof.

In some implementations, the visual display device 72 may be an integral component of the foot imaging apparatus 20. In such a case, the visual display screen 74 may be provided on an exterior surface of the foot imaging apparatus 20. Alternatively, in other embodiments, the visual display device 72 may be provided as an external standalone device wired and/or wirelessly connected to the foot imaging apparatus 20. Non-limiting examples of external standalone devices that can act as a visual display device in some implementations include televisions, laptop and desktop computers, flat panel display devices, smartphones, cell phones, tablet computers, personal digital assistants, and the like. The visual display screen 74 can use liquid crystal display (LCD), light-emitting diode (LED) technology, organic LED (OLED) technology, plasma display panel (PDP) technology or another appropriate display technology. Depending on the application or use, the monitoring image can be displayed on the visual display screen 74 either as still images or as a video stream. The monitoring image can be displayed in real-time or near real-time or be saved to memory for archival storage or later viewing and analysis.

In some implementations, the foot imaging apparatus 20 and/or the visual display device 72 can include a user interface (not shown) to allow a user or operator to act on the monitoring image displayed on the visual display screen 74. By way of example, in some implementations, the user interface can allow the user to control one or more image parameters including, without limitation, contrast, brightness, sharpness, color, zoom, panning, rotation, size and tilting. In some implementations, reference markers or features can be superimposed on the image to aid the determination and analysis of whether the foot is correctly positioned on the membrane. In some implementations, this determination and analysis can be partially or even fully automated, for example by using model-based anatomical and positional image recognition. In the case of a fully automated process, the monitoring and assessment of foot positioning could be performed without requiring human intervention.

Figure 14A:
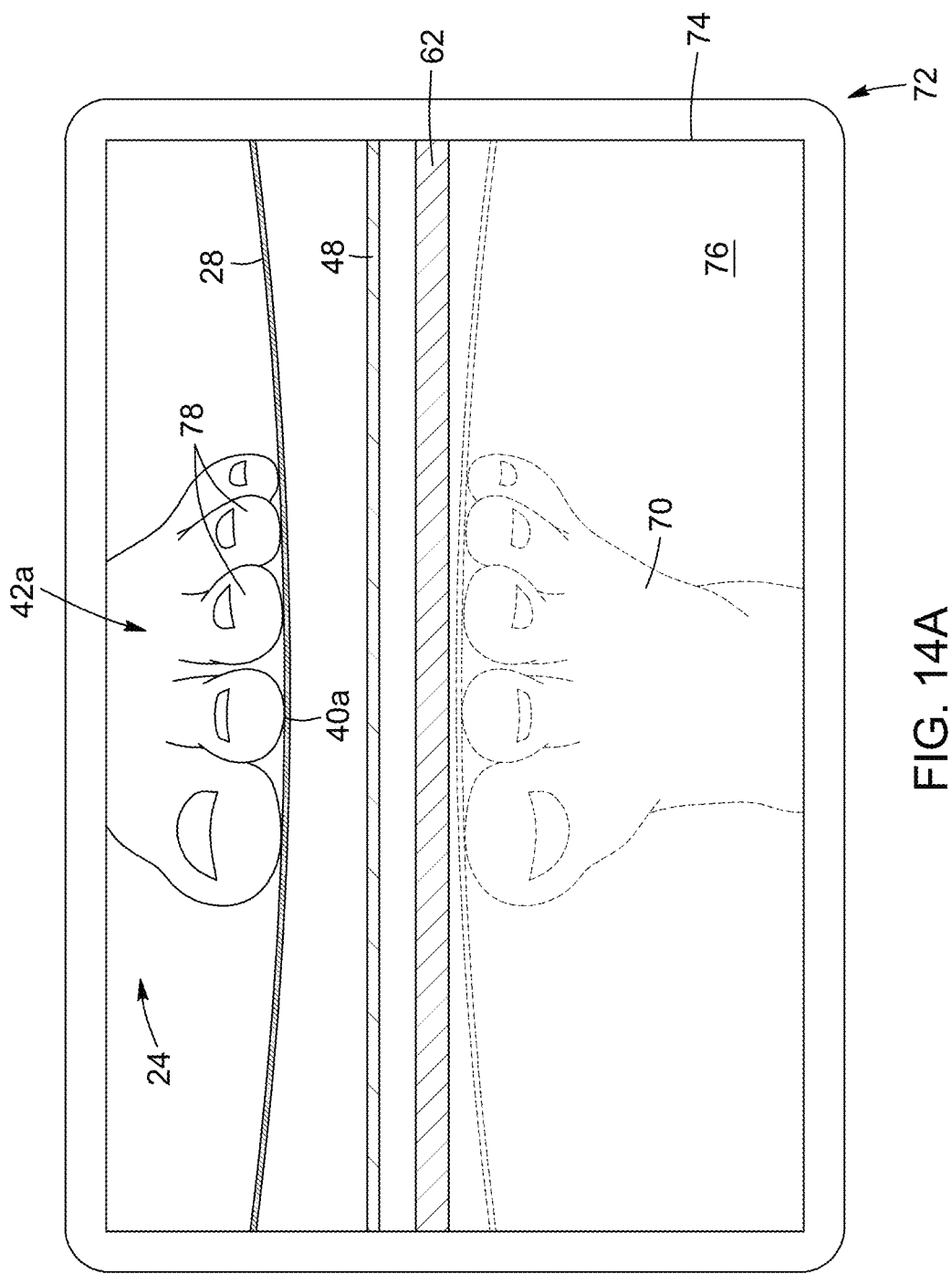
FIG. 14A is a representation of a visual display device displaying a monitoring image captured by the monitoring unit of an exemplary embodiment of a foot imaging apparatus and providing a front elevation view of the foot received on the membrane.
Figure 14B:
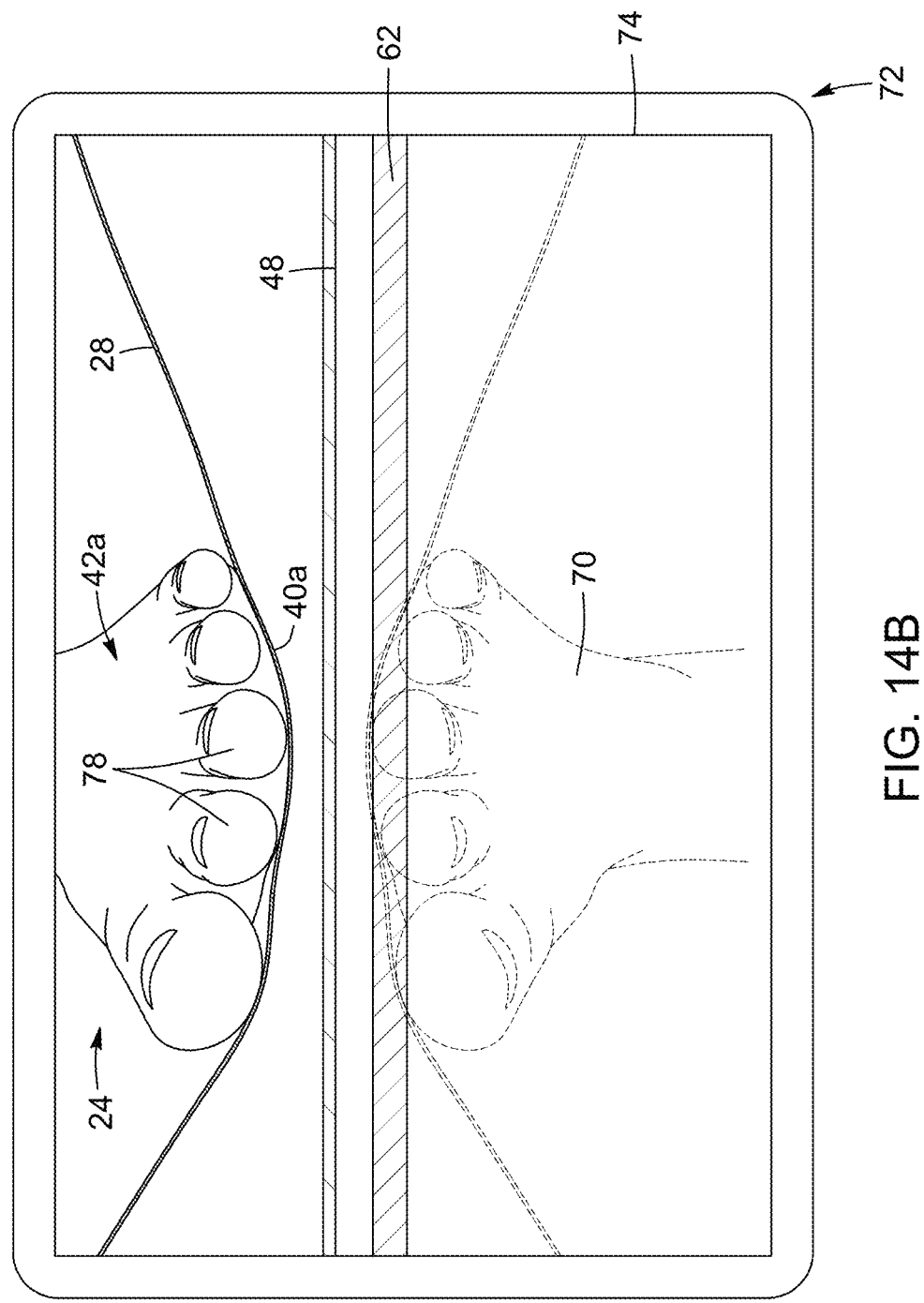
FIG. 14B is a representation of a visual display device displaying a monitoring image captured by the monitoring unit of an exemplary embodiment of a foot imaging apparatus and providing a front elevation view of the foot received on the membrane.
Figure 15A:
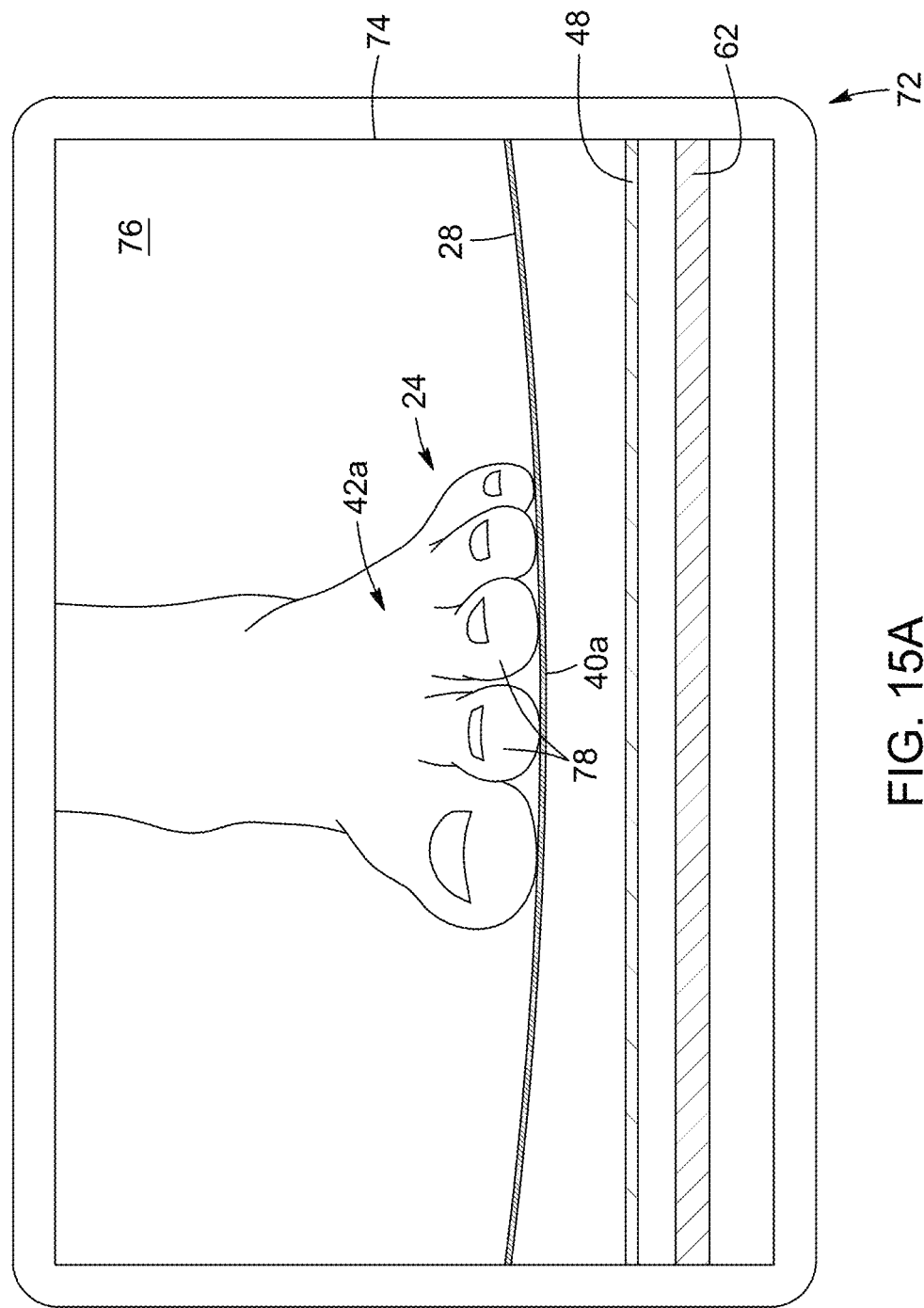
FIG. 15A is a representation of a visual display device displaying a monitoring image captured by the monitoring unit of an exemplary embodiment of a foot imaging apparatus and providing a front elevation view of the foot received on the membrane.
Figure 15B:
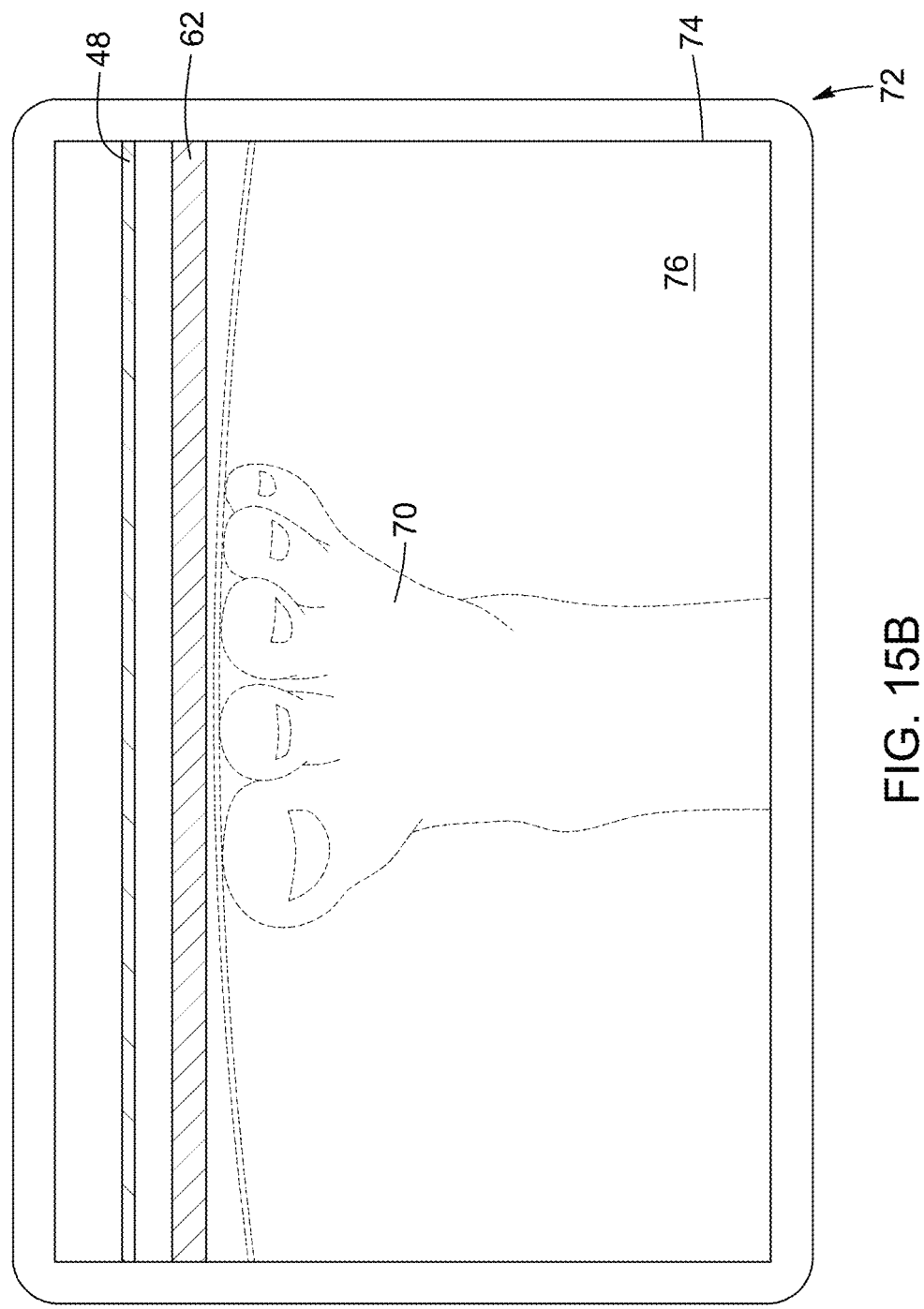
FIG. 15B is a representation of a visual display device displaying a monitoring image captured by the monitoring unit of an exemplary embodiment of a foot imaging apparatus and providing a front elevation view of the foot received on the membrane.

Referring to FIGS. 14A and 14B, there are shown schematic representations of exemplary monitoring images 76 that can be displayed on a visual display screen 74 of a visual display device 72. In FIGS. 14A and 14B, the monitoring unit is configured to monitor the front portion 42a of the foot 24, as in FIGS. 3 and 4. As mentioned above, monitoring the positioning of the front portion of the foot can be advantageous, especially under semi-weight bearing, because any significant forefoot deformation can have detrimental effects on the overall shape of the plantar surface and, potentially, degrade the reliability and accuracy of the 3D plantar image.

The monitoring image 76 in each of FIGS. 14A and 14B includes a depiction of both the membrane 28 itself with the foot 24 received thereon and a reflection 70 of the membrane 28. However, in other implementations, the field of view of the monitoring unit may be such that either the front portion 42a of the foot 24 or its reflection 70 is only partially visible in the monitoring image 76. In yet other implementations, such as those illustrated in FIGS. 15A and 15B, the monitoring image 76 displayed on the visual display screen 74 can show only the foot 24 on the membrane 28 (see FIG. 15A) or only a reflection 70 thereof (see FIG. 15B). It is noted that to more clearly depict the positioning of the foot 24, the membrane 28 has been assumed to be optically transparent in FIGS. 14A, 14B, 15A and 15B.

Figure 17:
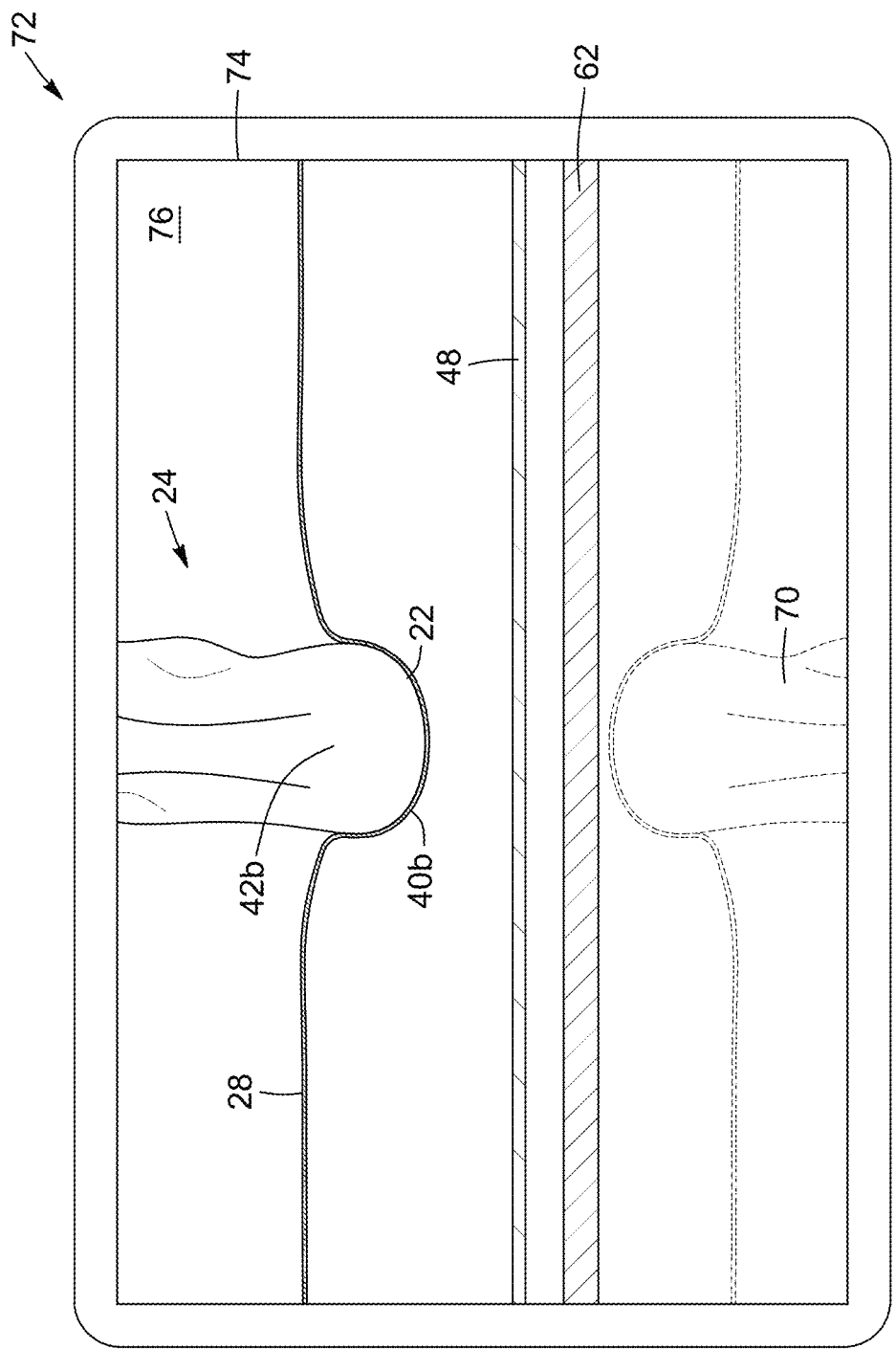
FIG. 17 is a representation of a visual display device displaying a monitoring image captured by the monitoring unit of an exemplary embodiment of a foot imaging apparatus and providing a rear elevation view of the foot received on the membrane.

In FIGS. 14A, 14B, 15A and 15B, the monitoring image 76 from which correct foot positioning can be assessed provides a front elevation view of the foot 24 received on the flexible membrane 28. However, as mentioned above, in other implementations the monitoring image 76 from which correct foot positioning can be assessed can provide a rear elevation view of the foot 24 received on the flexible membrane 28. This exemplary scenario is illustrated in FIG. 17, where the positioning of the foot 24 on the membrane 28 is correct.

Returning to FIGS. 14A and 14B, by analyzing the monitoring image 76, the operator (e.g., a podiatrist) can assess whether the foot 24 is properly positioned on the membrane 28 prior to, and optionally during, acquiring a 3D plantar image thereof. By way of example, in some implementations, the information about the positioning of the foot 24 received on the flexible membrane 28 can include one or more of the following information: a degree of flatness of a forefoot-receiving region 40a of the flexible membrane 28 with the foot 24 received thereon; a presence or absence of physical contact between the flexible membrane 28 with the foot 24 received thereon and an underlying solid surface; a degree of deformation of the front portion 42a of the foot 24 when the foot 24 is received on the flexible membrane 28; a degree of dorsiflexion of the toes 78 when the foot 24 is received on the flexible membrane 28; and a position of the foot 24 with respect to reference markers.

In FIG. 14A, the forefoot-receiving region 40a of the membrane 28 is under relatively high tension and presents a rather uniform and flat receiving surface to the front portion 42a of the foot 24. Thus, the front portion 42a of the foot 24 is positioned relatively flat and parallel to a horizontal reference plane and its deformation due to vertical and/or lateral compressive loads remains relatively small. Also, the toes 78 are not overly curled up, which otherwise could adversely deform the medial and lateral arches 80a, 80b of the foot 24 (see FIG. 6) and deleteriously affect the image acquisition process. It can therefore be concluded that the position of the patient's foot 24 on the flexible membrane 28 is correct and indicative that a satisfactory semi-weight-bearing state has been reached, and that a 3D plantar image can be acquired.

By contrast, in FIG. 14B, the front portion 42a of the foot 24 is significantly deformed and off-position, with the whole foot 24 being off-centered widthwise (i.e., to the left in FIG. 14B) and the toes 78 being overly dorsiflexed (i.e., curved upwardly). It can therefore be concluded that the position of the patient's foot 24 on the flexible membrane 28 is incorrect and that an adequate semi-weight-bearing state has not been reached. In such a case, the position of the patient's foot 24 on the flexible membrane 28 can be adjusted and monitored until the foot's position is satisfactory for the image acquisition process.

Figure 16:
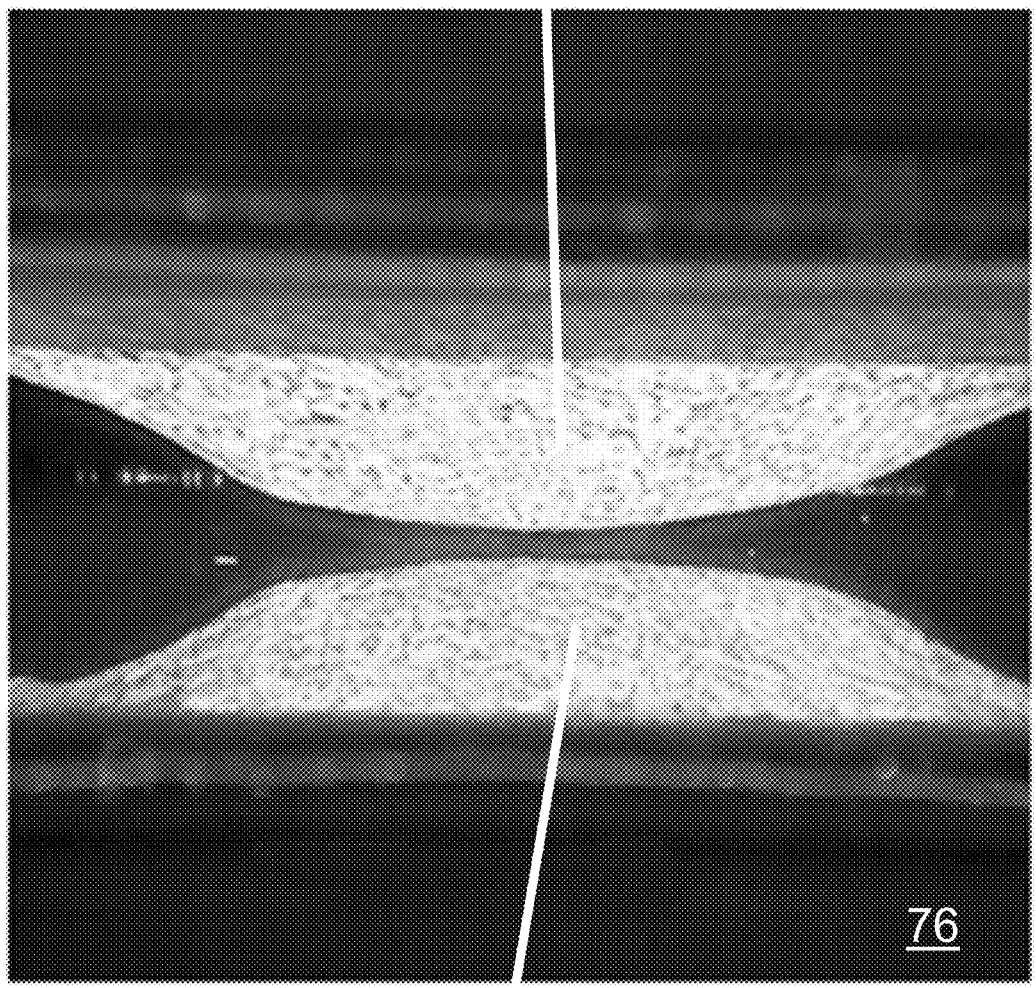
FIG. 16 is an actual image acquired by the monitoring unit of an exemplary embodiment of a foot imaging apparatus. The image shown in FIG. 16 depicts both the foot-receiving membrane itself with the foot received thereon and a reflection of the foot-receiving membrane off an underlying reflective surface.

Referring now to FIG. 16, there is depicted an actual image 76 acquired by the monitoring unit of a foot imaging apparatus, in accordance with an exemplary embodiment.

The image 76 depicts both the foot-receiving membrane 28 with the foot received thereon and a reflection 70 of the membrane 28 off an underlying reflective surface. It is noted that the foot itself is not directly visible in FIG. 16 due to the membrane 28 being opaque in the illustrated embodiment.

Foot Imaging Method

Figure 18:
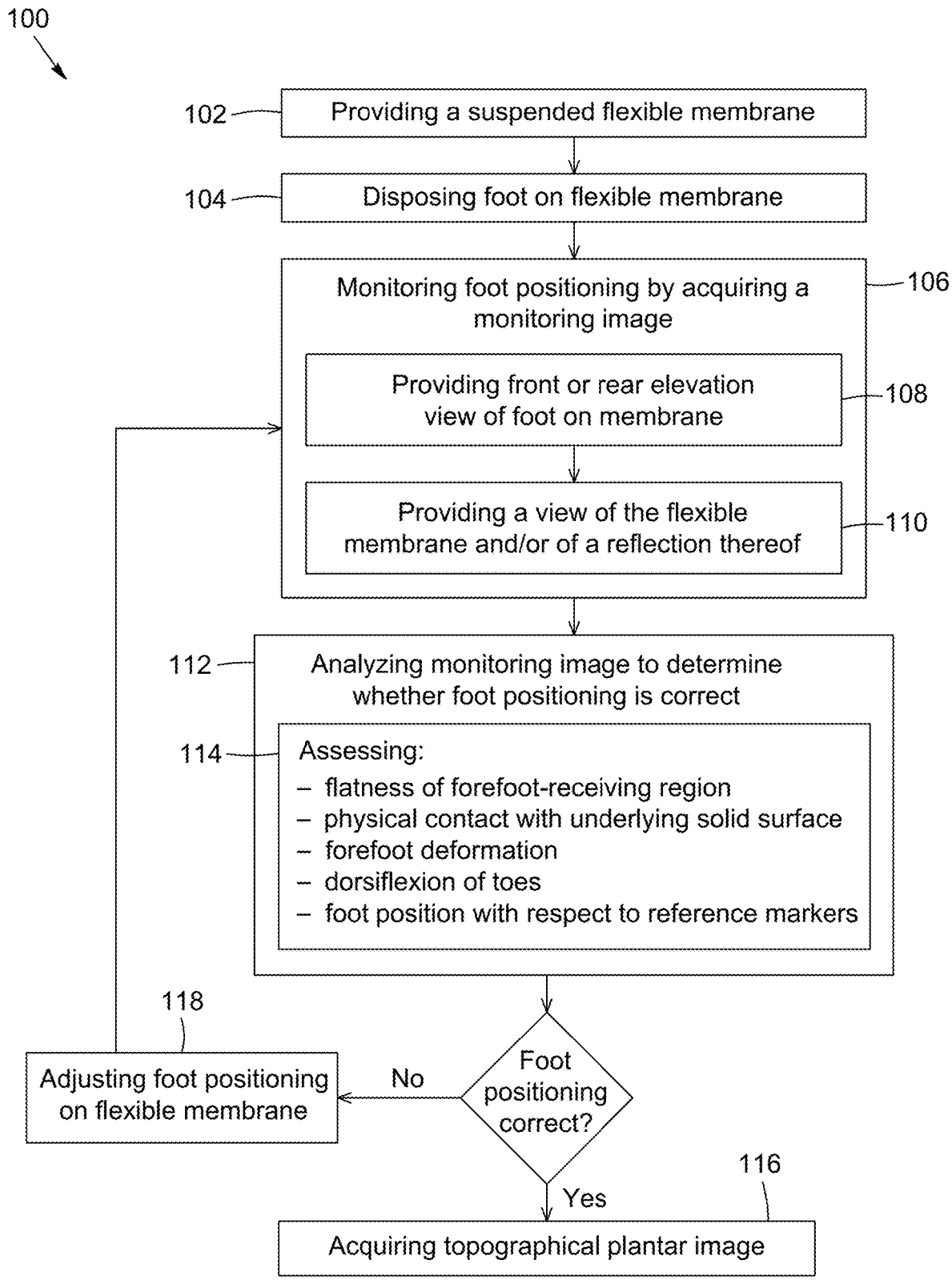
FIG. 18 is a flow chart of a method for imaging a foot, in accordance with an exemplary embodiment.

In accordance with another aspect, there is provided a method for imaging a foot. Referring to FIG. 18, there is provided a flow chart of an exemplary embodiment of such a method 100. By way of example, the method 100 shown in FIG. 18 can be performed with a foot imaging apparatus including a monitoring unit such as those described above, or with another apparatus. The foot imaging method described herein generally involves performing a monitoring of a foot received and supported on a suspended membrane of a 3D foot imaging apparatus to ensure or help ensure that the foot is correctly positioned on the membrane in view of carrying out the image acquisition steps of the method.

Referring to FIG. 18, the method 100 first includes a step 102 of providing a suspended flexible membrane. The flexible membrane can enclose an upper portion of an inflatable chamber, as described above with respect to the foot imaging apparatus. The membrane may, but need not, have a rear end elevated relative to a front end thereof. The membrane includes a forefoot-receiving region and a rearfoot-receiving region respectively affixed to a front end and a rear end of the support structure, respectively. In some implementations, the rearfoot-receiving region can be under less tension than the forefoot-receiving region. Such a configuration can be advantageous when the image of the foot is to be captured in a semi-weight bearing state. Exemplary techniques for achieving less tension in the rearfoot-receiving region are mentioned above. In some implementations, the step 102 of providing the flexible membrane can include securing the flexible membrane to the support structure.

In scenarios where the flexible membrane encloses part of an inflatable chamber, the method 100 can include a step of increasing the internal pressure in the inflatable chamber, for example until an internal pressure threshold is reached. The value of the internal pressure threshold can be determined such as to induce a deformation of the foot received on the flexible membrane that leads to a semi-weight-bearing state in which the foot arches and the heel are properly enveloped by the flexible membrane. The internal pressure threshold can be determined by the operator or user (e.g., podiatrist, podiatric physician, or healthcare professional) manually sensing the internal pressure in the pressure chamber or based on pressure data provided by a pressure sensor operatively connected to the inflatable chamber. The internal pressure threshold can also be predetermined, based on, for example and without limitation, patient's characteristics, the elasticity of the membrane and/or the inclination angle of the suspended membrane.

Referring still to FIG. 18, the method 100 then includes a step 104 of disposing the foot on the membrane, for example in a semi-weight-bearing condition. In embodiments where the foot is disposed on the membrane in a semi-weight-bearing condition, the entire plantar surface of the foot can be received on and supported by the flexible membrane, without contact with other physical parts or components (e.g., an underlying solid surface). In some implementations, the foot of the patient is positioned on the flexible membrane by the operator. The operator can manipulate the patient's foot to ensure that it is configured in the semi-weight-bearing condition. By way of example, in a non-limitative embodiment, the operator can perform one or more of the following manipulations:

moving the foot vertically downward onto the membrane with the front and the rear portions of the foot received in the forefoot- and rearfoot-receiving regions of the membrane, respectively;

setting at or near 90° the angle between the foot and the tibia, the angle between the tibia and the femur, and the angle between the femur and the torso, while keeping the foot, the tibia and the femur in a same vertical plane;

adjusting the internal pressure of the inflatable chamber, for example based on the rigidity of the foot;

positioning the subtalar joint in a neutral position;

exerting a downwardly directed force on the patient's knee to achieve a desired semi-weight-bearing state; and maintaining the desired semi-weight-bearing state while acquiring the 3D plantar image.

As mentioned above, achieving proper foot positioning (e.g., in a semi-weight-bearing state) can be difficult in practice as the foot, notably the shape of the forefoot, is generally not readily visible to the operator during the foot positioning and image capture process. To this end, the method 100 of FIG. 18 includes a step 106 of monitoring a positioning of the foot on the membrane, the monitoring including acquiring a monitoring image indicative of or containing information about the positioning of the foot on the membrane. By way of example, the monitoring image can be acquired using a monitoring unit such as described above. In some implementations, monitoring images can be acquired in real-time with the foot positioned on the membrane and be displayed as a video stream on a display screen. In other implementations, one or a series of still monitoring images can be acquired and visually displayed to the operator. In some implementations, acquiring the monitoring image can include a step 108 of providing one of a front elevation view and a rear elevation view of the foot received on the flexible membrane. Additionally, or alternatively, acquiring the monitoring image can include a step 110 of providing at least one of a view of the flexible membrane with the foot thereon and a view of a reflection of the flexible membrane with the foot thereon.

Referring still to FIG. 18, once the monitoring image or images have been captured, the method 100 can include a step 112 of analyzing the monitoring image to determine whether the positioning of the foot on the membrane is correct. As mentioned above, the analysis of the monitoring image to assess adequate foot positioning on the membrane can be based on various tests, criteria, factors, pass levels, and thresholds, each of which may be objective (quantitative) or subjective (qualitative). Non-limiting examples of criteria that can be assessed to determine whether the foot is positioned correctly on the membrane can include a step 114 of assessing at least one of: a degree of flatness of a forefoot-receiving region of the flexible membrane with the foot received thereon; a presence or absence of physical contact between the flexible membrane with the foot received thereon and an underlying solid surface; a degree of deformation of the front portion of the foot when the foot is received on the flexible membrane; a degree of dorsiflexion of the toes when the foot is received on the flexible membrane; and a position of the foot with respect to reference markers.

In some implementations, if the positioning of the foot on the membrane is deemed to be correct, the method 100 can include a step 116 of acquiring a topographical plantar image of the foot received on the membrane.

However, if the positioning of the foot on the membrane is deemed to be incorrect, the method 100 can include a step 118 of adjusting the positioning of the foot on the flexible membrane, followed by a step of iteratively repeating the monitoring 106, analyzing 112 and adjusting 118 steps until the positioning of the foot on the membrane is correct. In some implementations, the adjusting step can include one or more of the following: (i) displacing the foot on the membrane; (ii) increasing or decreasing the pressure in the inflatable chamber (manually or automatically); (iii) adjusting the downwardly directed force on the foot when the foot is received on the flexible membrane; and (iv) applying a compressive load on the flexible membrane along a peripheral portion of the forefoot-receiving region.

Once proper foot positioning has been achieved, the topographical plantar image of the foot received on the membrane can be captured. Depending on the application or use, it may be desirable to continue monitoring foot positioning during the image acquisition process, especially if the image acquisition process is not nearly instantaneous (e.g., if the process lasts more than a few seconds).

In some implementations, the captured monitoring images may not be displayed prior to the 3D image acquisition process, but may instead be stored in a memory for later viewing and analysis. For example, in some implementations, monitoring images can be compared with corresponding 3D plantar images to study and establish relationships between incorrect foot positioning in the monitoring images and its repercussions on the quality of the 3D plantar images.

Of course, numerous modifications could be made to the embodiments described above without departing from the scope of the present description.

The invention claimed is:

1. A foot imaging apparatus comprising:
    a housing comprising a top wall, a bottom wall spaced apart from the top wall, and a sidewall interconnecting the top wall and the bottom wall, the top wall defining an opening;
    a support structure coupled with the top wall along a periphery of the opening;

a flexible membrane suspended from the support structure and extending across the opening, the flexible membrane and the housing defining an inflatable chamber, the flexible membrane being configured, upon inflation of the inflatable chamber, to receive a foot thereon;

a three-dimensional (3D) imager configured to acquire a topographical plantar image of the foot on the flexible membrane from under the flexible membrane; and a monitoring unit configured to monitor a monitored region in order to evaluate a positioning of the foot received on the flexible membrane upon inflation of the inflatable chamber, the monitoring unit comprising a camera configured to acquire a monitoring image of the monitored region, the monitoring image containing information about the positioning of the foot received on the flexible membrane and corresponding to one of a front elevation view and a rear elevation view of the foot received on the flexible membrane, wherein at least a portion of the monitoring unit is arranged within the inflatable chamber.

2. The foot imaging apparatus of claim 1, wherein the monitoring unit further comprises at least one light deflector arranged to deflect light from the monitored region into a field of view of the camera for capture by the camera as the monitoring image, wherein the at least one light deflector is included in the portion of the monitoring unit arranged within the inflatable chamber.

3. The foot imaging apparatus of claim 2, wherein the camera and the at least one light deflector are arranged with respect to the flexible membrane such that the monitoring image provides at least one of a view of the flexible membrane with the foot thereon and a view of a reflection of the flexible membrane with the foot thereon.

4. The foot imaging apparatus of claim 2, wherein the bottom wall is mounted on a top surface of the 3D imager, the at least one light deflector is located inside the housing, and the camera is located inside the 3D imager and configured to acquire the monitoring image through the bottom wall of the housing and the top surface of the 3D imager.

5. The foot imaging apparatus of claim 2, wherein the at least one light deflector is a plane mirror lying at least partly in the field of view of the camera.

6. The foot imaging apparatus of claim 5, wherein the plane mirror has a surface normal that is oriented at a tilt angle with respect to an axis of the field of view of the camera.

7. The foot imaging apparatus of claim 6, wherein the tilt angle ranges from 30° to 60°.

8. The foot imaging apparatus of claim 7, wherein the tilt angle is equal to 45°.

9. The foot imaging apparatus of claim 6, wherein the axis of the field of view of the camera points vertically upward.

10. The foot imaging apparatus of claim 2, wherein the portion of the monitoring unit arranged within the inflatable chamber further includes the camera.

11. The foot imaging apparatus of claim 1, wherein the 3D imager is located inside the housing.

12. The foot imaging apparatus of claim 1, wherein the monitoring image is a still image.

13. The foot imaging apparatus of claim 1, wherein the monitoring image is a video stream.

14. The foot imaging apparatus of claim 1, further comprising a visual display device configured to display the monitoring image acquired by the camera.

15. The foot imaging apparatus of claim 1, wherein the information about the positioning of the foot received on the flexible membrane comprises one or more of the following:

a degree of flatness of a forefoot-receiving region of the flexible membrane with the foot received thereon;

a presence or absence of physical contact between the flexible membrane with the foot received thereon and an underlying solid surface;

a degree of deformation of the front portion of the foot when the foot is received on the flexible membrane;

a degree of dorsiflexion of the toes when the foot is received on the flexible membrane; and a position of the foot with respect to reference markers.

16. The foot imaging apparatus of claim 1, wherein the flexible membrane is configured to receive the foot thereon in a semi-weight-bearing condition.

17. The foot imaging apparatus of claim 1, wherein the portion of the monitoring unit arranged within the inflatable chamber includes the camera.

18. A membrane assembly comprising:

a housing having a top wall, a bottom wall, and a sidewall interconnecting the top and bottom walls, the top wall having an opening therein;

a support structure arranged along a periphery of the opening;

a flexible membrane suspended from the support structure and extending across the opening, the flexible membrane and the housing defining an inflatable chamber, the flexible membrane being configured, upon inflation of the inflatable chamber, to receive a foot thereon; and a monitoring unit configured to monitor a monitored region in order to evaluate a positioning of the foot received on the flexible membrane upon inflation of the inflatable chamber, the monitoring unit comprising a camera configured to acquire a monitoring image of the monitored region, the monitoring image containing information about the positioning of the foot received on the flexible membrane and corresponding to one of a front elevation view and a rear elevation view of the foot received on the flexible membrane, wherein at least a portion of the monitoring unit is arranged within the inflatable chamber.

19. The membrane assembly of claim 18, wherein the monitoring unit further comprises at least one light deflector arranged to deflect light from the monitored region into a field of view of the camera for capture by the camera as the monitoring image, wherein the at least one light deflector is included in the portion of the monitoring unit arranged within the inflatable chamber.

20. The membrane assembly of claim 19, wherein the portion of the monitoring unit arranged within the inflatable chamber further includes the camera.

21. The membrane assembly of claim 18, wherein the portion of the monitoring unit arranged within the inflatable chamber includes the camera.

22. A method for imaging a foot, comprising the steps of:

providing a suspended flexible membrane, the flexible membrane defining an upper portion of an inflatable chamber;

adjusting an internal pressure of the inflatable chamber to inflate the inflatable chamber including the flexible membrane;

disposing the foot on the flexible membrane;

monitoring, via a monitoring unit comprising a camera, a positioning of the foot received on the flexible membrane upon inflation of the inflatable chamber, comprising acquiring a monitoring image containing information about the positioning of the foot received on the flexible membrane and corresponding to one of a front elevation view and a rear elevation view of the foot received on the flexible membrane, wherein acquiring the monitoring image includes acquiring the monitoring image via the monitoring unit having at least a portion arranged within the inflatable chamber;

analyzing the monitoring image to determine whether the positioning of the foot on the flexible membrane is correct; and if the positioning of the foot on the flexible membrane is correct, acquiring, from under the flexible membrane, a topographical plantar image of the foot received on the flexible membrane; otherwise, adjusting the positioning of the foot on the flexible membrane and repeating the monitoring, analyzing and adjusting steps until the positioning of the foot on the flexible membrane is correct.

23. The method of claim 22, wherein acquiring the monitoring image comprises providing at least one of a view of the flexible membrane with the foot thereon and a view of a reflection of the flexible membrane with the foot thereon.

24. The method of claim 22, wherein analyzing the monitoring image comprises assessing at least one of:

a degree of flatness of a forefoot-receiving region of the flexible membrane with the foot received thereon;

a presence or absence of physical contact between the flexible membrane with the foot received thereon and an underlying solid surface;

a degree of deformation of the front portion of the foot when the foot is received on the flexible membrane;

a degree of dorsiflexion of the toes when the foot is received on the flexible membrane; and a position of the foot with respect to reference markers.

25. The method of claim 22, wherein the portion of the monitoring unit arranged within the inflatable chamber includes the camera.

26. The method of claim 22, wherein the monitoring unit further comprises at least one light deflector arranged within the inflatable chamber, and acquiring the monitoring image via the monitoring unit comprises deflecting, via the least one light deflector, light from the monitored region into a field of view of the camera for capture by the camera as the monitoring image.

27. The method of claim 26, wherein the portion of the monitoring unit arranged within the inflatable chamber further includes the camera.

* * * * *